United States Patent [19]
Altdorf et al.

[11] Patent Number: 6,019,744
[45] Date of Patent: Feb. 1, 2000

[54] TAMPON APPLICATOR

[75] Inventors: Rolf Altdorf, Brennofen; Axel Friese, Wuppertal; Georg Weihrauch, Waldmichelbach, all of Germany; Ted Foley, East Brunswick, N.J.; Raymond Hull, Hampton, N.J.; Gerd Rex, Somerset, N.J.

[73] Assignee: McNeil-PPC, Inc., Skillman, N.J.

[21] Appl. No.: 08/114,422

[22] Filed: Aug. 30, 1993

Related U.S. Application Data

[63] Continuation of application No. 07/846,770, Mar. 6, 1992, abandoned, which is a continuation of application No. 07/737,822, Jul. 29, 1991, abandoned, which is a continuation of application No. 07/495,788, Mar. 22, 1990, abandoned.

[30] Foreign Application Priority Data

Mar. 31, 1989 [DE] Germany .............................. 39 10 458

[51] Int. Cl.$^7$ .................................................... A61F 13/20
[52] U.S. Cl. ............................... 604/16; 604/18; 604/904
[58] Field of Search ................................ 604/11, 13–18, 604/904

[56] References Cited

U.S. PATENT DOCUMENTS

| | | |
|---|---|---|
| 3,103,929 | 9/1963 | Brecht . |
| 4,286,595 | 9/1981 | Ring . |
| 4,291,696 | 9/1981 | Ring . |
| 4,573,963 | 3/1986 | Sheldon ................................. 604/15 |
| 4,699,610 | 10/1987 | Hanano et al. ........................... 604/16 |
| 4,857,044 | 8/1989 | Lennon . |
| 4,891,042 | 1/1990 | Melvin et al. . |
| 4,911,687 | 3/1990 | Stewart et al. ........................... 604/15 |
| 4,960,417 | 10/1990 | Tarr et al. ................................ 604/15 |

FOREIGN PATENT DOCUMENTS

| | | |
|---|---|---|
| 344 312 | 7/1978 | Austria . |
| 836423 | 1/1976 | Belgium . |
| 0 291 343 | 11/1988 | European Pat. Off. . |
| GM 7442182 | 4/1975 | Germany . |
| 35 40 725 | 5/1986 | Germany . |
| 3540725 | 5/1986 | Germany . |
| 2 204 491 | 11/1988 | United Kingdom . |
| 2204491 | 11/1988 | United Kingdom . |
| 2 220 359 | 1/1990 | United Kingdom . |
| 2220359 | 1/1990 | United Kingdom . |

Primary Examiner—Ronald K. Stright, Jr.

[57] ABSTRACT

The invention relates to a tampon applicator having a cylindrical outer sleeve and an inner sleeve, which is displaceable therein, is provided with an axial longitudinal slit and encloses a tampon. A tongue-shaped retention element is integrally connected to the outer sleeve so as to be bendable and projects through the longitudinal slit of the inner sleeve into the latter, and lies against the rear end of the tampon. When the inner sleeve is withdrawn out of the outer sleeve, the tampon is held in place by the retention element and transferred into the outer sleeve. The retention element is provided with one part of a locking mechanism (detent plate), the other part of which is formed by one of the two sleeves (longitudinal edges of the longitudinal slit of the inner sleeve. The aforesaid locking parts interact in such a way that the retention element is locked in its engaged position bent into the inner sleeve. The transfer of the tampon out of the inner sleeve into the outer sleeve is thereby ensured when the tampon applicator is utilized, and at the same time a simple, economic mass production of the tampon regulator is ensured.

17 Claims, 17 Drawing Sheets

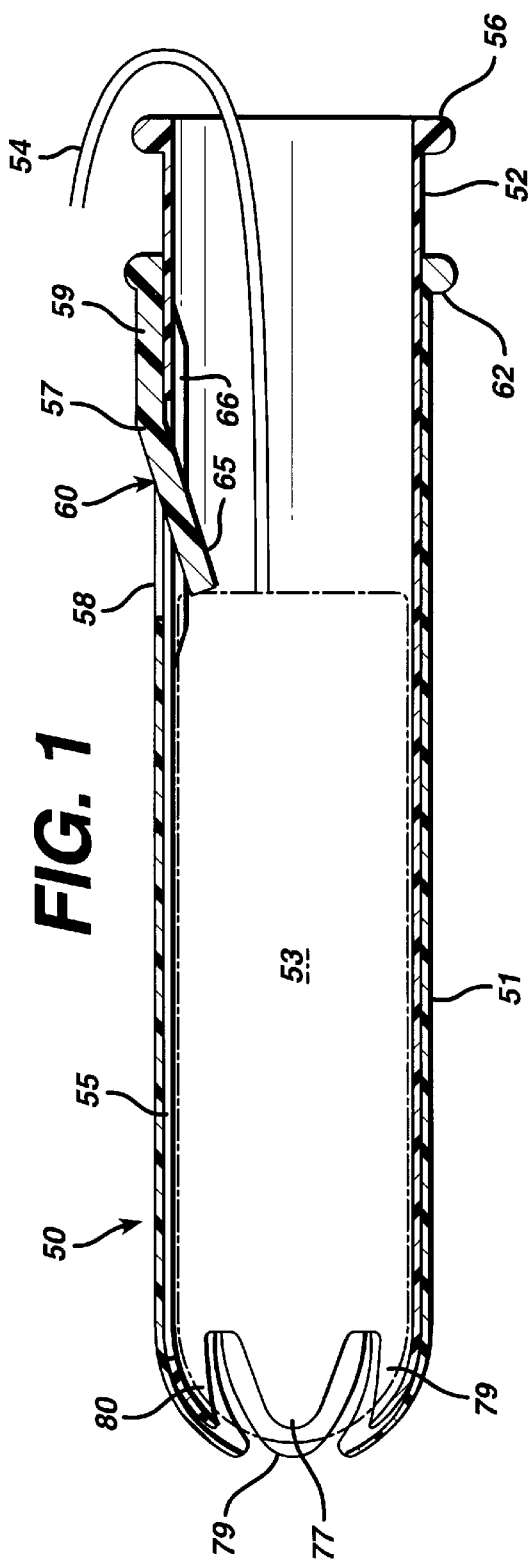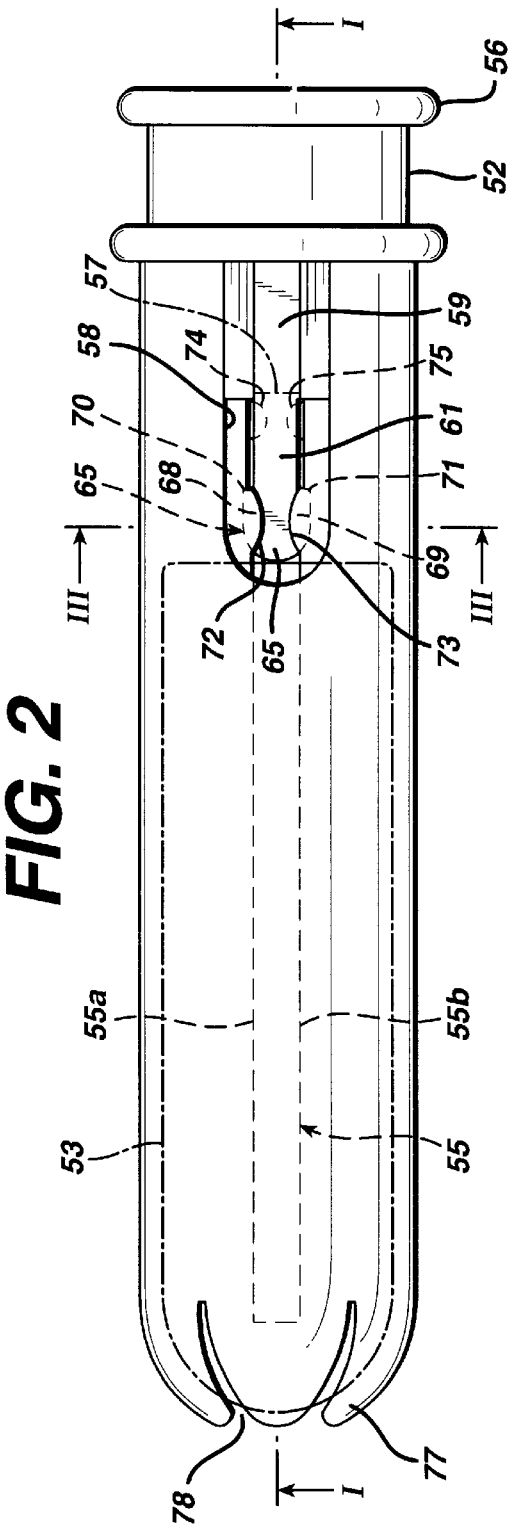

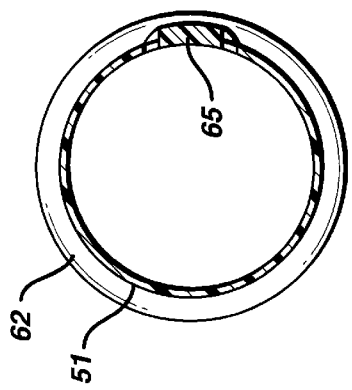
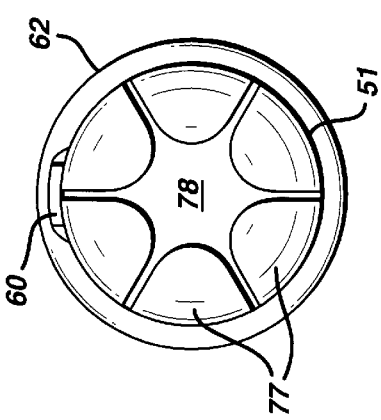
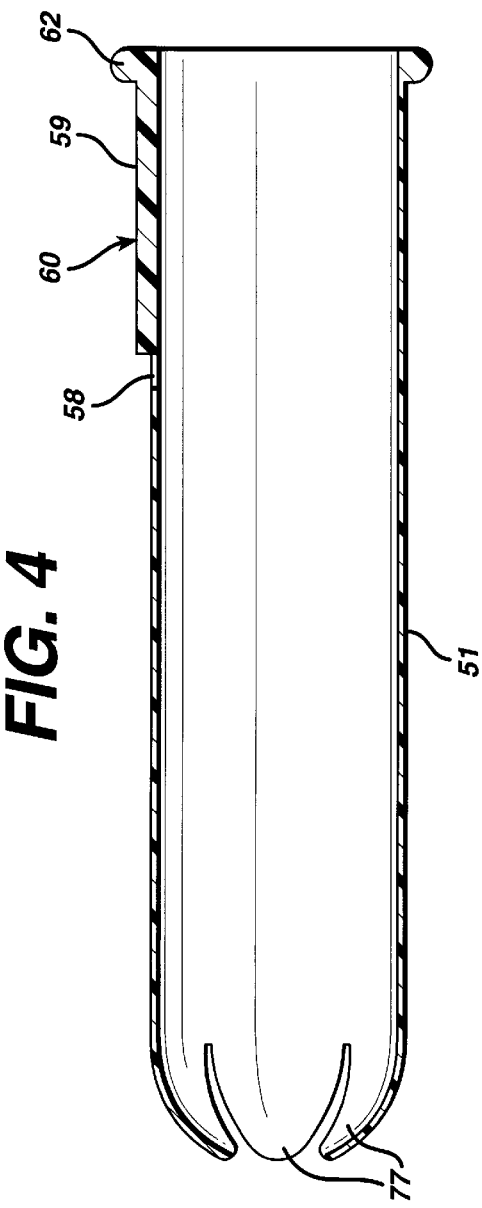
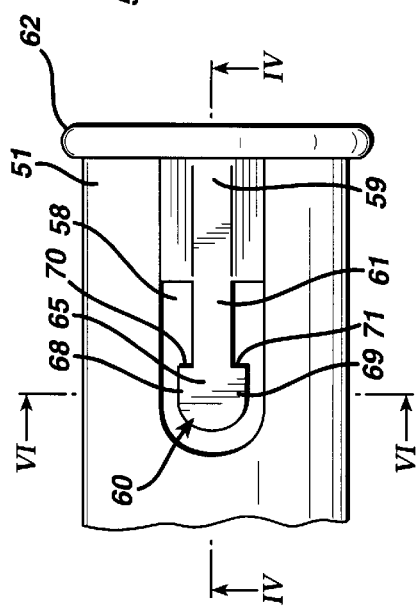

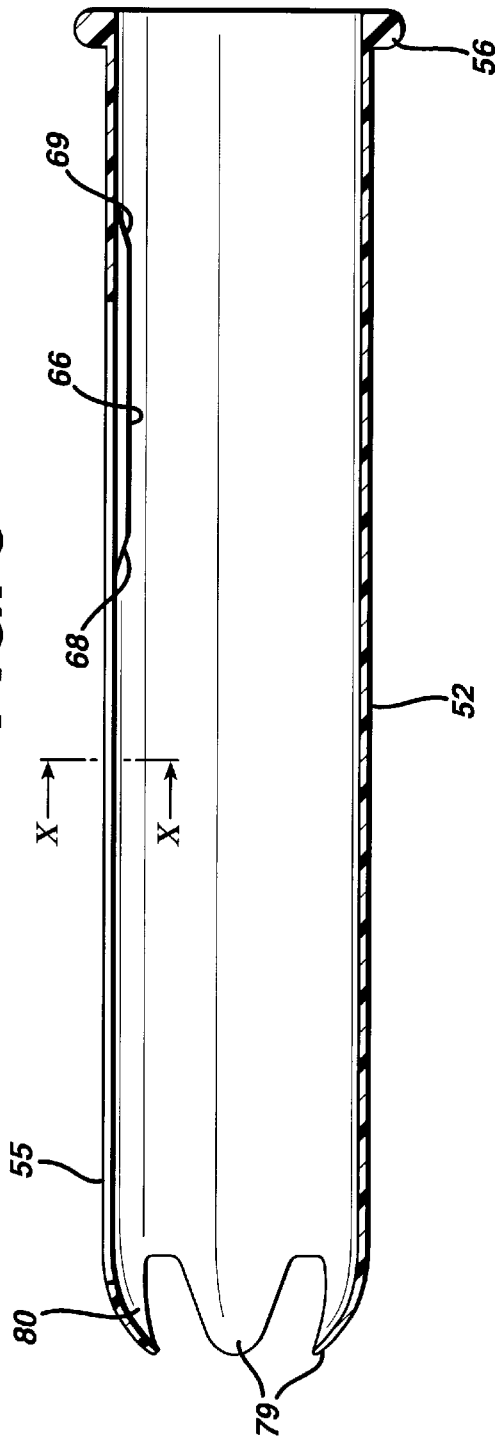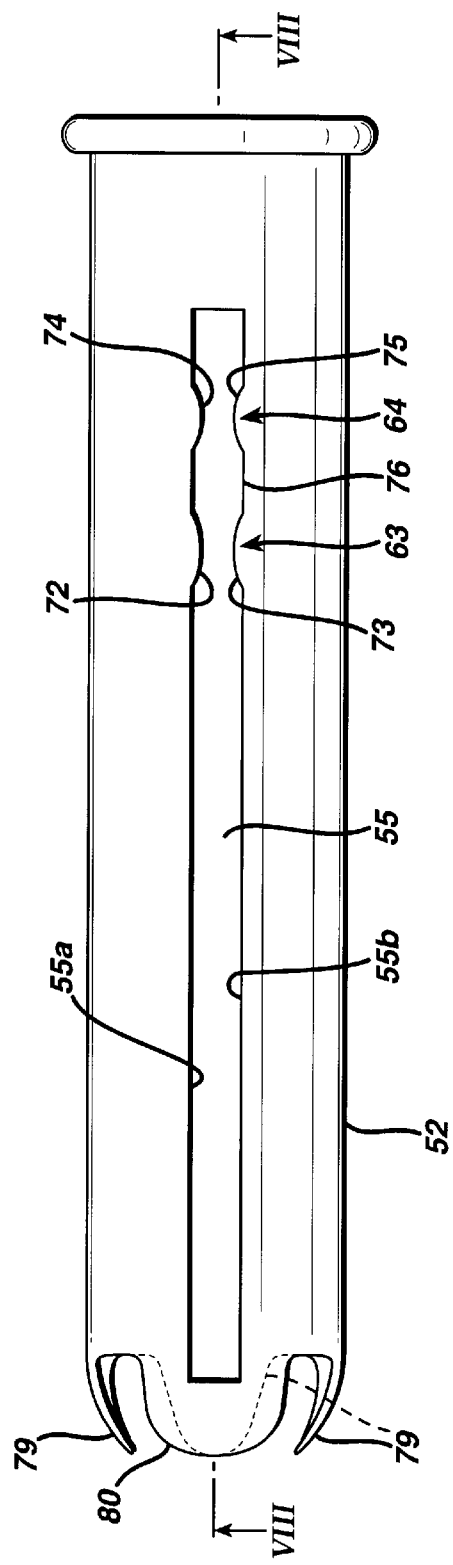

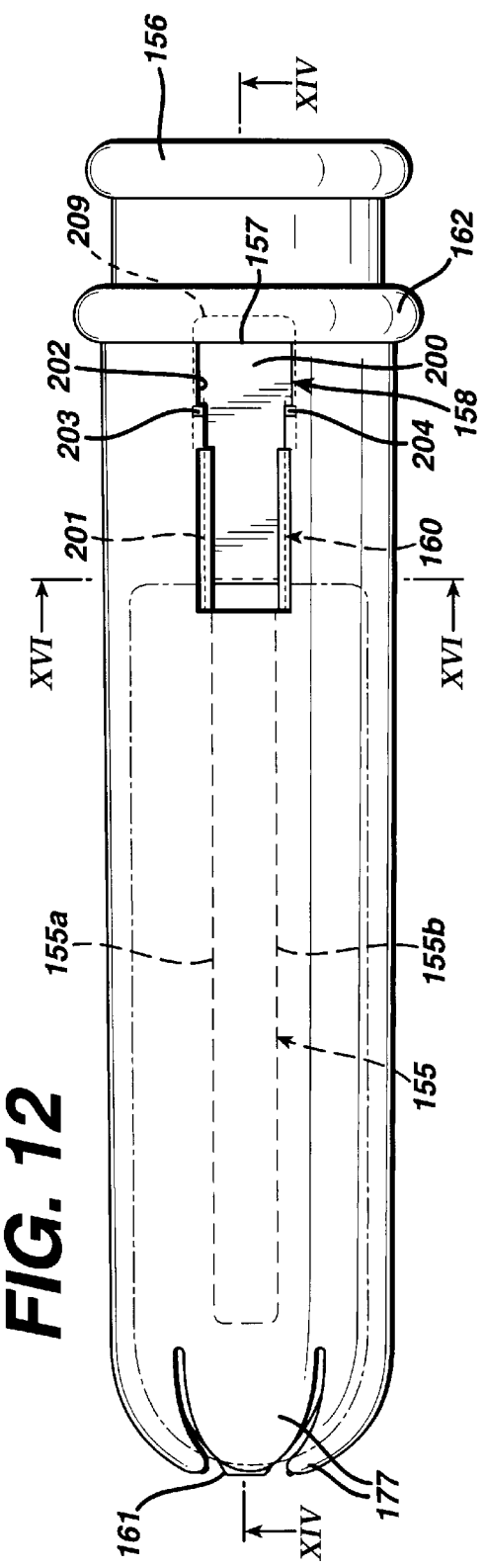
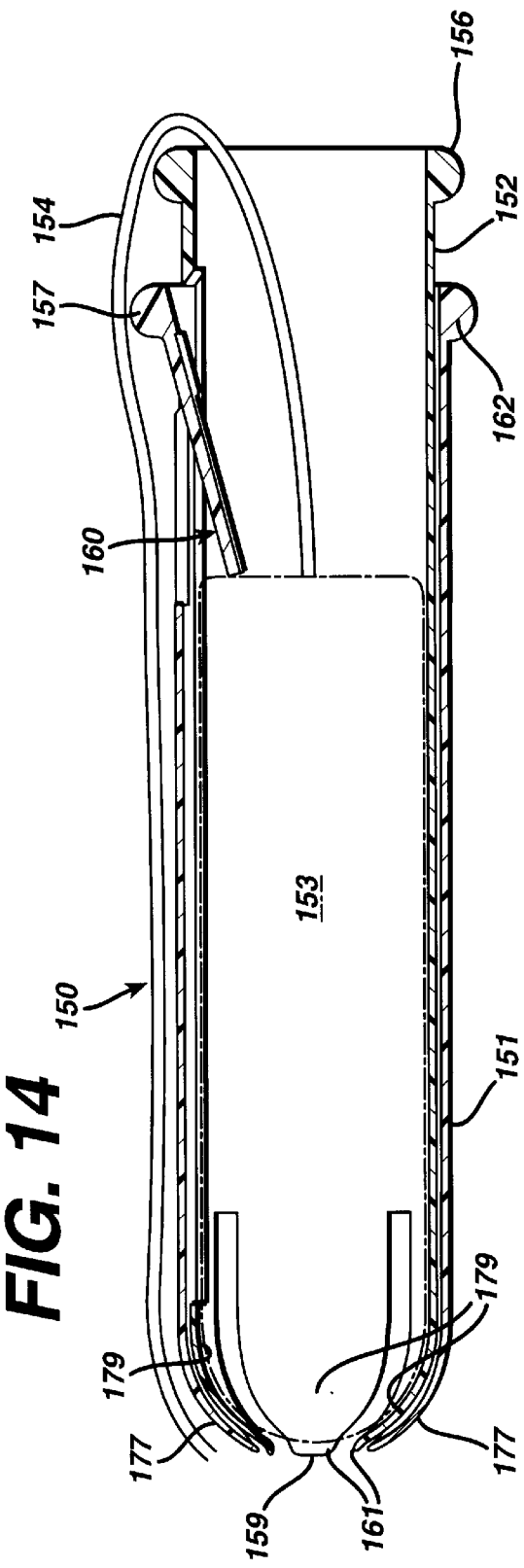

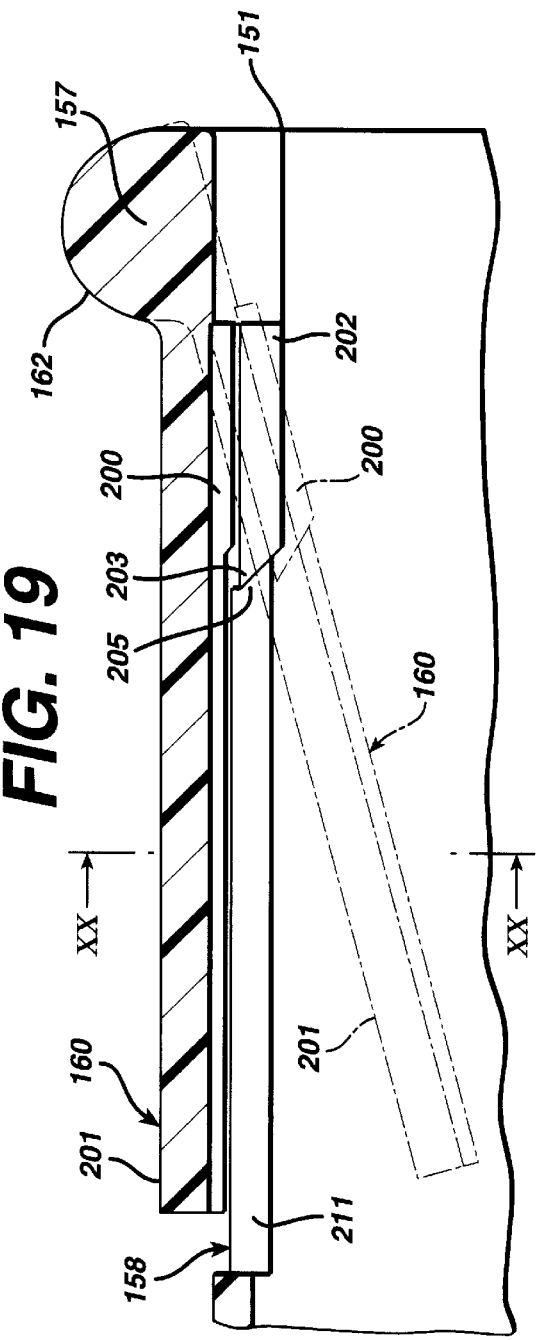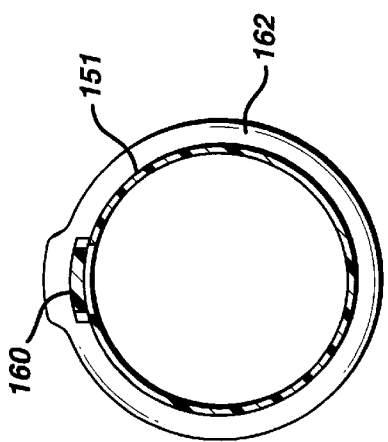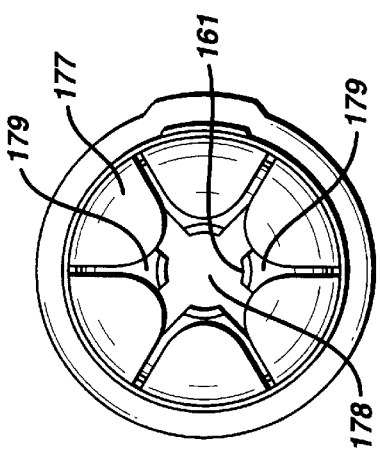

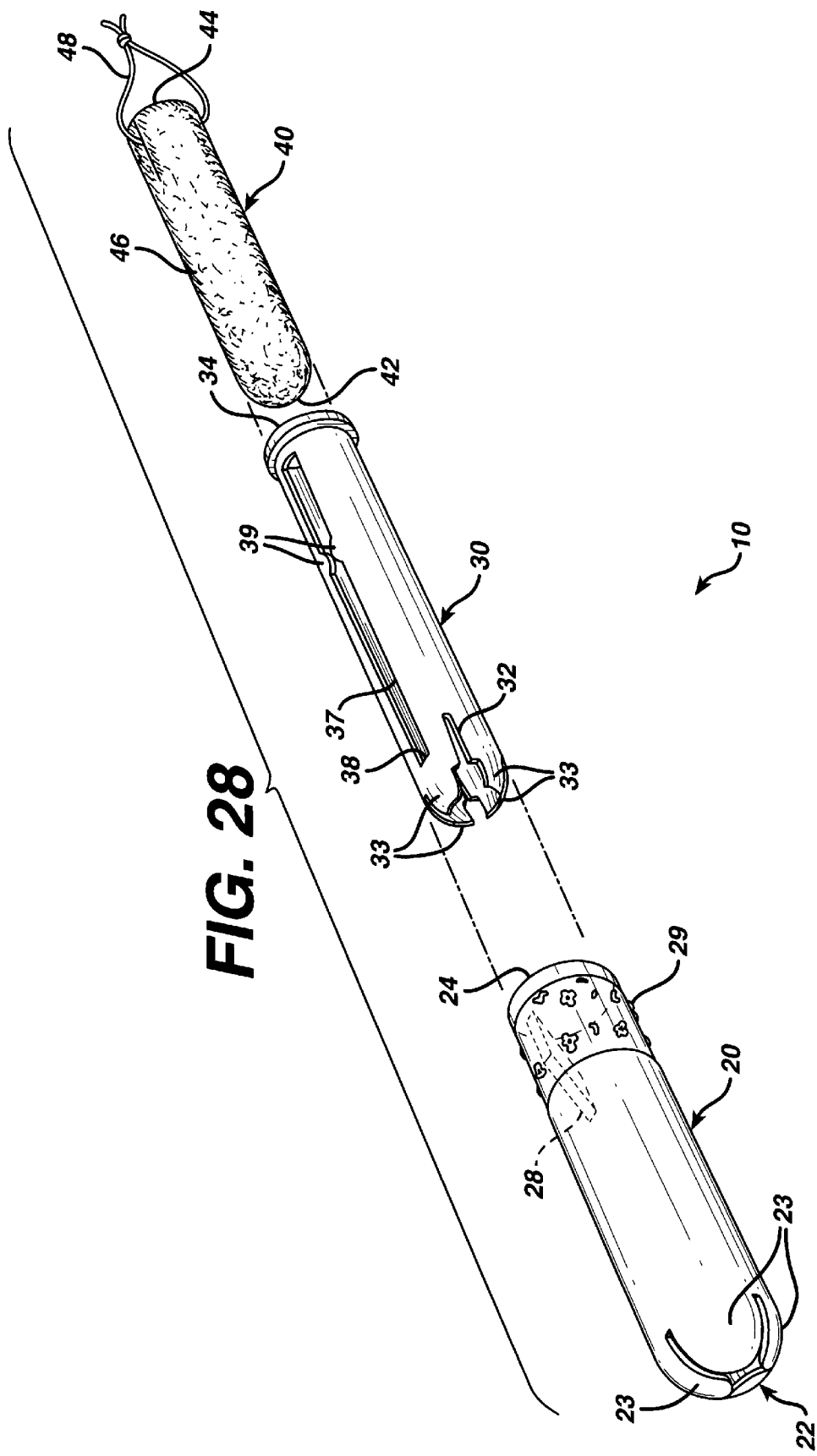

TAMPON APPLICATOR

This a continuation of application Ser. No. 07/846,770, filed Mar. 6, 1992, now abandoned, which is a continuation of Ser. No. 07/737,822 filed Jul. 29, 1991, now abandoned, which is a continuation of Ser. No. 07/495,788, filed Mar. 22, 1990, now abandoned, which is hereby incorporated by reference.

This application claims the benefit of priority of German Patent Application No. P 39 10 458 "Tampon Applicator", filed Mar. 31, 1989, the content of which is hereby incorporated herein by reference.

BACKGROUND OF THE INVENTION

This invention relates to tampon applicators and, more particularly, to improved collapsible tampon applicators.

In the past, catemenial tampons have been applied and used either with or without applicators. For example, digital tampons are inserted into the vaginal cavity manually. Applicators, however, have been used in order to facilitate the insertion of the tampon and for the purposes of comfort and discretion. Generally, tampon applicators are composed of two separate concentric plastic or cardboard tubes in telescopic relationship to one another. The tube having a larger diameter cross-section is termed the outer sleeve, which generally retains the tampon plug, or absorbent element. The tube having a smaller diameter is the "inner sleeve" and is usually positioned within of the outer sleeve behind the tampon plug. The inner sleeve expels the tampon plug from the applicator during use.

Tampon applicators have been with the inner and outer sleeves separated into two pieces, such that the tampons require assembly when the woman uses the tampon. Although the packages are smaller prior to use, such packaging entails the disadvantage of requiring the consumer to assemble the product.

Some collapsible tampon applicator designs use a tampon plug composed of high density absorbent material having a mushroom-like dome shape at the end which is first inserted into the body. The inside surface of the outer sleeve of the tampon contains small nibs which protrude inward and hold the tampon plug in place while the inner sleeve is extended. This construction has several disadvantages. High density plugs are hard and uncomfortable to wear. Moreover, they do not absorb fluid as quickly as low density materials. Furthermore, a mushroom-shaped tampon plug cannot be replaced into the tampon applicator should the user err in dispensing the plug.

Thus, a tampon applicator is needed that is easy to use, discrete, comfortable and flexible enough to allow for the expansion of a low density tampon within it.

A tampon applicator of the collapsible design is known from German Utility Model 7,442,182, in which the retention element consists of a tongue pushed out from the body of the outer sleeve, which tongue is formed from plastic integrally with the outer sleeve and is brought into the desired bent position by corresponding heat treatment.

U.S. Pat. No. 4,286,595 describes a tampon applicator in which a projection is connected to the inner wall of the outer sleeve. This projection grips under the longitudinal edges of a longitudinal slit in the inner sleeve of the applicator. The longitudinal slit extends at a distance between the front and rear end of the inner sleeve, so that the inner sleeve is held captively by the projection. The front end of the projection lies against the rear end of the tampon, so that the inner sleeve can be withdrawn out of the outer sleeve in order to transfer the tampon into the outer sleeve.

An object of this invention is to improve a tampon applicator of the known generic type mentioned at the beginning in such a way that the transfer of the tampon out of the inner sleeve into the outer sleeve is ensured when the tampon applicator is utilized, and at the same time a simple and thus economic manufacture of the tampon applicator is ensured, which permits a mass production of the tampon applicator.

By expedient matching of the form of the retention element and of the longitudinal slit in the inner sleeve of the product of this invention, it is thus achieved that the retention element is mechanically arrested so that its contact position at the end of the tampon is exactly defined and can be maintained permanently. This ensures that, although the retention element can give way outwards when the inner sleeve is charged with a tampon, it then returns reliably into its contact position at the end of the tampon, and a reliable transfer of the tampon out of the inner sleeve into the outer sleeve is at all times ensured by the mechanically secured engaged position of the retention element. The simple design of the components of the tampon applicator, and the possibility of assembly it easily and quickly ensures an economic mass production of the tampon applicator.

The locking mechanism of the tampon applicator of this invention preferably consists of mutually overlapping parts of the retention element and at least one of the two sleeves, the parts overlapping one another in the unlocked state and gripping under one another in a locking manner in the locked state. Moreover, the invention permits an optional reinforcement of the retention element with respect to the thickness of the wall of the outer sleeve, so that the retention element itself exhibits a high bending or buckling strength.

In accordance with one embodiment of the invention, the retention element may be locked with the inner sleeve, the locking part of the retention element consisting of a detent plate which is dimensioned wider than the longitudinal slit in the inner sleeve. In this case, the detent plate is connected to the rear part of the outer sleeve so as to be bendable. The rear part of the outer sleeve is expediently stiffened by an external rib which extends between a rear, toroidal grip and the rear end of the through-opening of the outer sleeve. The retention element is advantageously formed as a continuation of the reinforcing rib.

Two longitudinal segments in the rear part of the longitudinal slit in the inner sleeve may be dimensioned narrower than the shank of the retention element, the longitudinal segment lying between the two longitudinal segments having a normal width and receiving the shank of the retention element in the outer sleeve in the pushed-in position of the inner sleeve.

Spreader strips may protrude inwards from the inside of the parallel longitudinal edges of the rear part of the longitudinal slit and reinforce the spreading away of the detent plate of the retention element into the interior of the inner sleeve.

The longitudinal slit in the inner sleeve extends into a resilient lip at the front end of the inner sleeve, this lip being dimensioned wider than the through-opening for the retention element in the outer sleeve in comparison to further lips extending with regular spacing over the periphery of the front end of the inner sleeve.

In a second embodiment of the invention, the retention element extends in the unlocked state from a toroidal grip, forming the bending axis of the retention element, at the rear end of the outer sleeve freely forwards outside a through-opening in the outer sleeve paraxially to the latter and has in its base region a detent plate as the locking part which interacts with rim parts of a through-opening at least in the outer sleeve as the other locking part. In this case the detent plate of the retention element may advantageously be dimensioned longer, but narrower, than an associated widened cut-out of the through-opening in the outer sleeve. The shoulders of the detent plate and the relatively, shorter length of the cut-out and the outer sleeve overlap one another in the unlocked state; in the locked state the shoulders of the detent plate grip under the shoulders of the outer sleeve with locking effect. The shoulder faces lying opposite one another are expediently designed to be slanted. A detent tongue extending forwards from the detent plate, and extends into the interior of the inner sleeve through the longitudinal slit thereof.

In the case where it is desirable to fix the inner sleeve essentially non-displaceably with respect to the outer sleeve before the tampon is inserted into the tampon applicator, the longitudinal segment, extending forwards from the cut-out for the detent plate, of the longitudinal slit in the inner sleeve may be dimensioned narrower than the detent tongue of the retention element of the outer sleeve, in such a manner that the inner sleeve is held friction-tightly against the detent tongue of the outer sleeve. In other circumstances it may also be desirable to dimension the longitudinal slit of the inner sleeve wider than the detent plate of the retention element along its entire length.

It is usually advisable to provide, in a manner known per se, the tampon applicator, both at the front end of the inner sleeve and also of the outer sleeve, with lips which are directed towards the central longitudinal axis of the sleeves and which are outwardly arcuate. In this case, a particularly advantageous measure consists in providing the lips of the inner sleeve with front lips which, in the position where the inner sleeve is pushed into the outer sleeve, grip under the front end of the lips of the outer sleeve. This ensures that the tampon can only be pushed out of the applicator if it has previously left the inner sleeve completely.

The invention is explained in greater detail below with reference to the diagrammatic drawings of two exemplary embodiments of a tampon applicator, in which:

FIG. 1 shows a first embodiment of a tampon applicator in a central longitudinal section I—I in FIG. 2;

FIG. 2 shows a plan view of the tampon applicator with retention element in FIG. 1;

FIG. 4 shows a central longitudinal section IV—IV of the outer sleeve of the tampon applicator in FIG. 5;

FIG. 5 shows a plan view of the outer sleeve in FIG. 4, in partially cutaway representation;

FIG. 6 shows a cross-section VI—VI in FIG. 5;

FIG. 7 shows a front view of the outer sleeve according to FIG. 4;

FIG. 8 shows the inner sleeve of the tampon applicator in FIGS. 1 and 2 in a central longitudinal section VIII—VIII in FIG. 9;

FIG. 9 shows a plan view of the inner sleeve according to FIG. 8;

FIG. 12 shows a second embodiment of a tampon applicator with retention element in plan view;

FIG. 14 shows a central longitudinal section XIV—XIV in FIG. 12;

FIG. 17 shows a front view of the tampon applicator in FIG. 12;

FIG. 19 shows a central longitudinal section XIX—XIX in FIG. 18, the retention element being shown in the angled retention position in phantom representation;

FIG. 20 shows a cross-section XX—XX in FIG. 19;

FIG. 21 shows a section XXI—XXI in FIG. 18;

Figure 22:
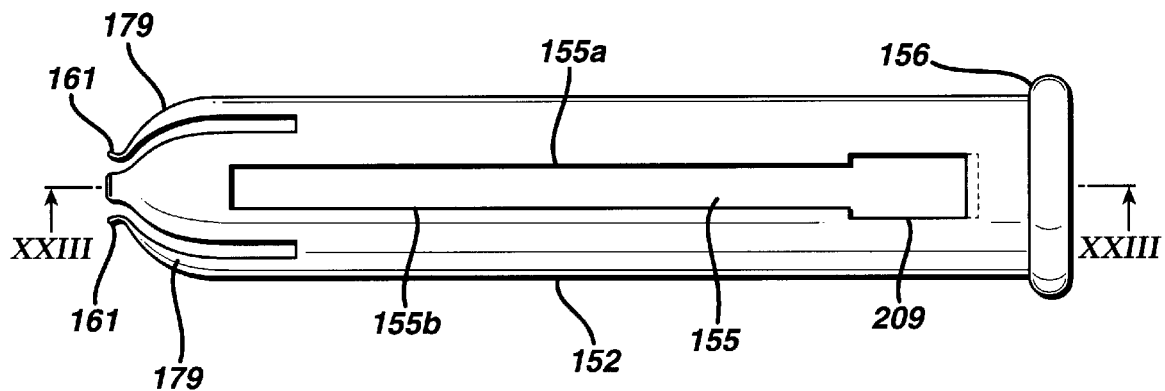
FIG. 22 shows a plan view of the inner sleeve of the second embodiment according to FIG. 12.
Figure 22A:
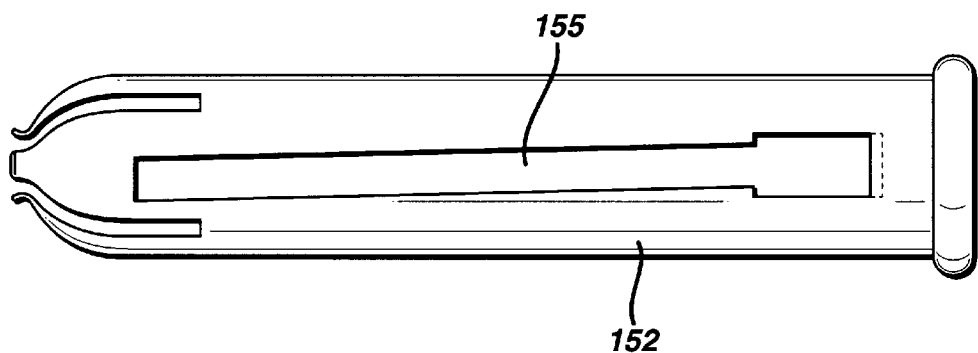

FIG. 22*a* shows a plan view of the inner sleeve of an alternative embodiment having an angled slit.

Figure 13:
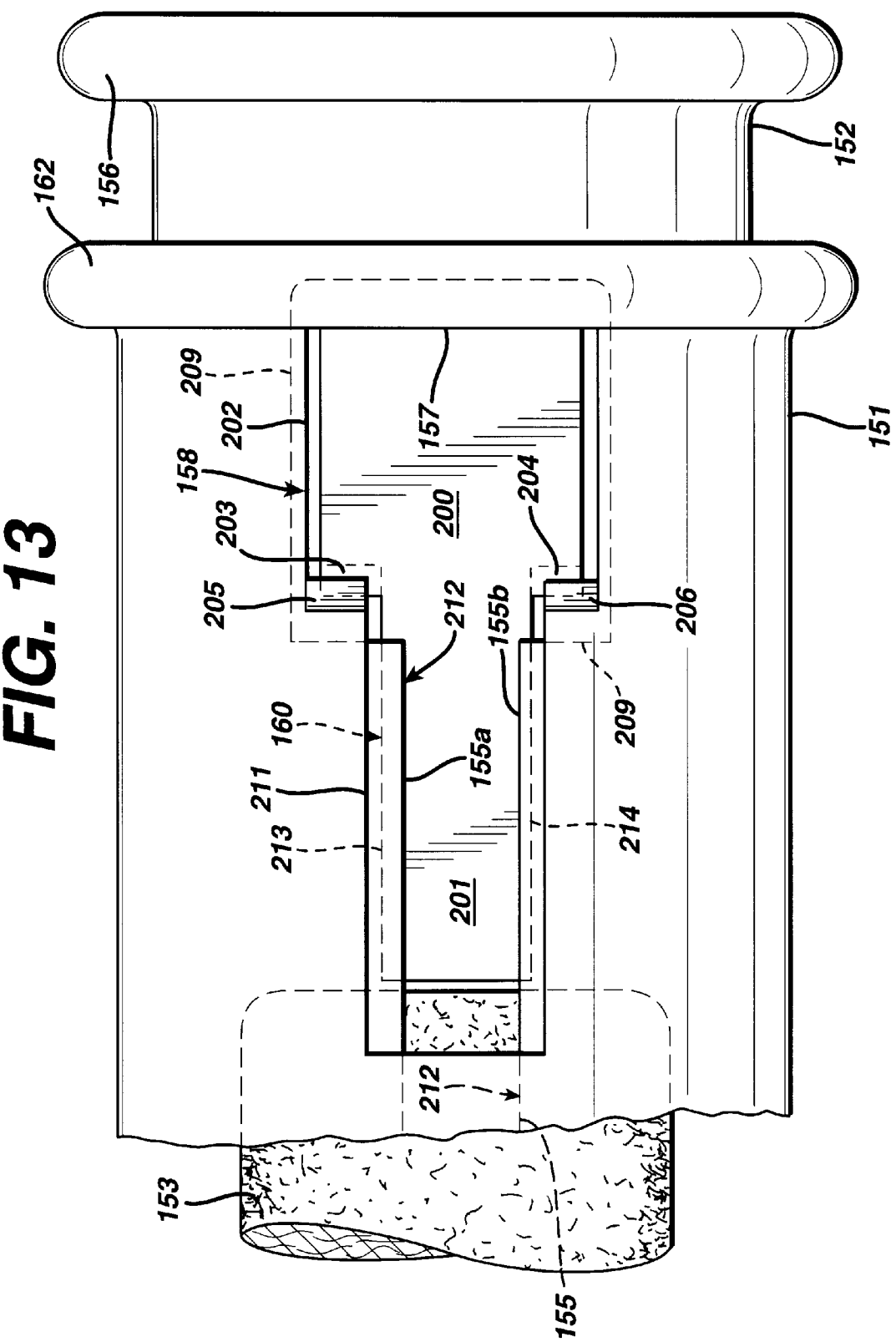
FIG. 13 shows the locked retention plate in FIG. 12 on an enlarged scale.
Figure 23:
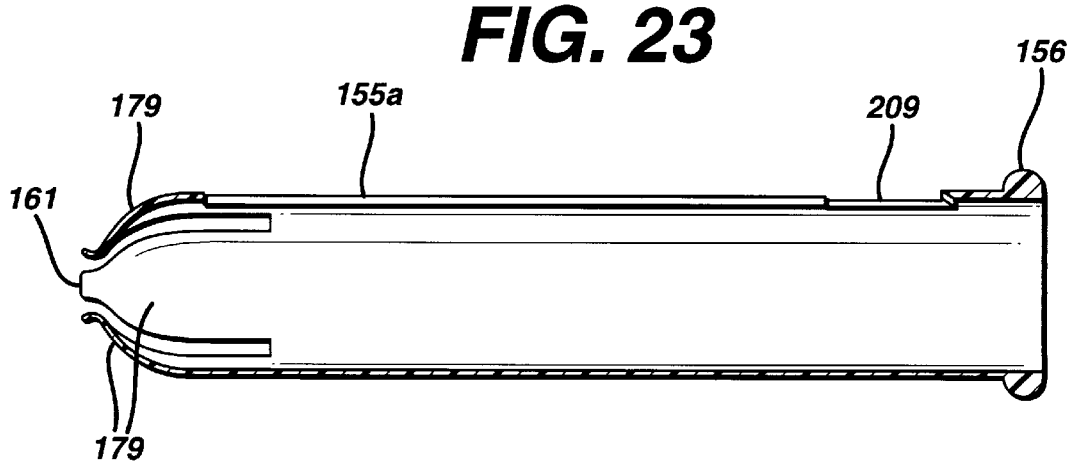
Figure 24:
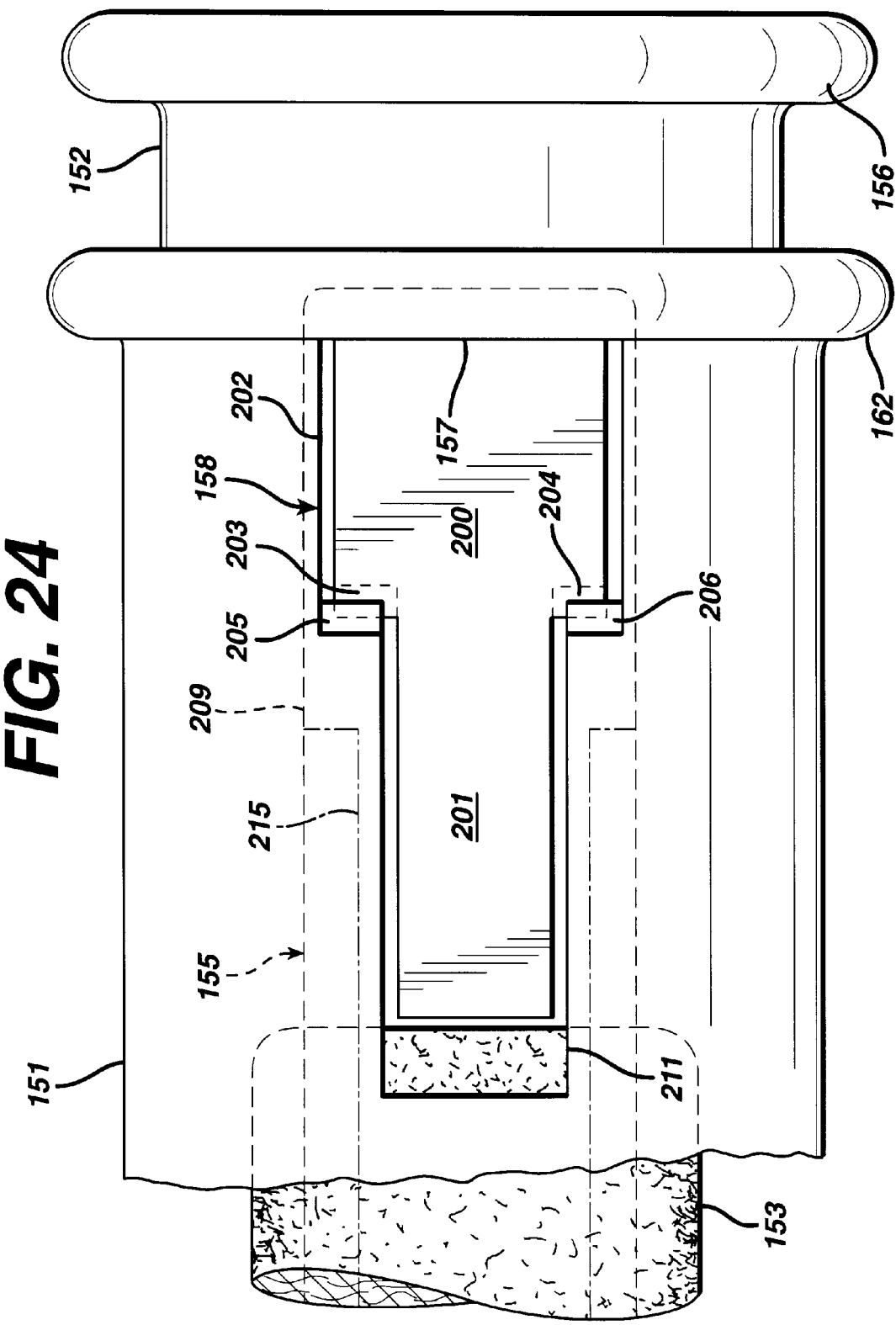

FIG. 23 shows a central longitudinal section XXIII—XXIII in FIG. 22;

FIG. 24 shows a view as FIG. 13, but with a longitudinal slit of the same width in the inner sleeve.

Figure 25A:
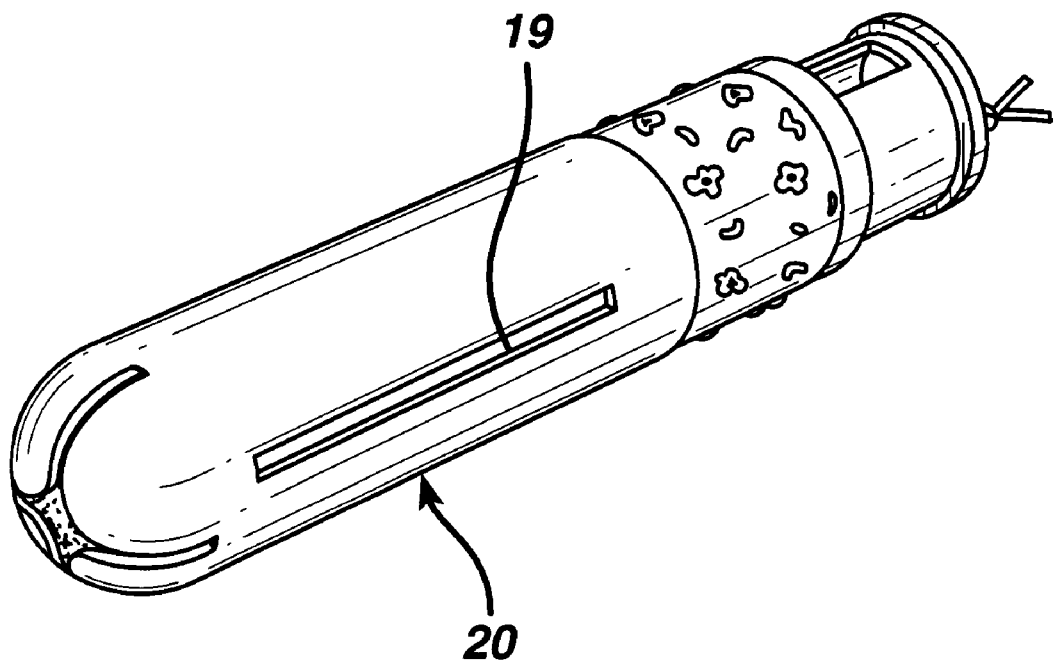
Figure 25:
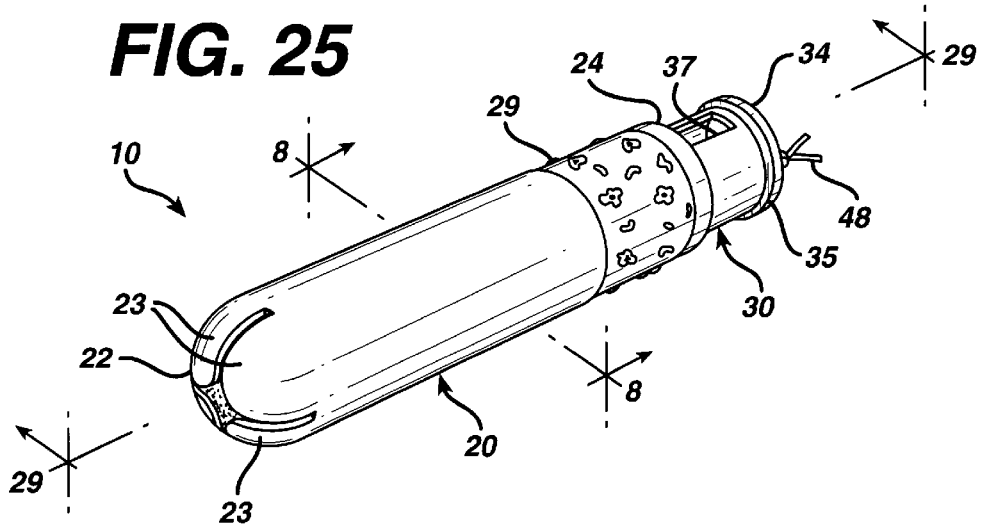

FIG. 25 is a perspective view of the tampon applicator when the inner sleeve is moved toward the rear end while still substantially inside the outer sleeve and still surrounding the tampon;

FIG. 25*a* shows a perspective view of the outer sleeve of an alternative embodiment having a longitudinal slit.

Figure 26:
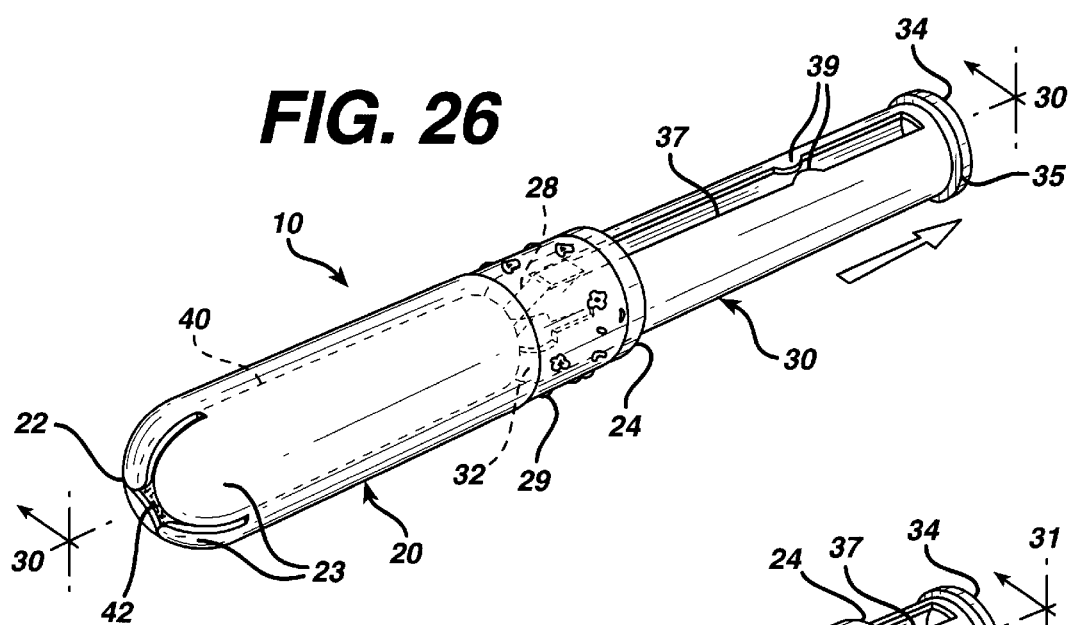
Figure 27:
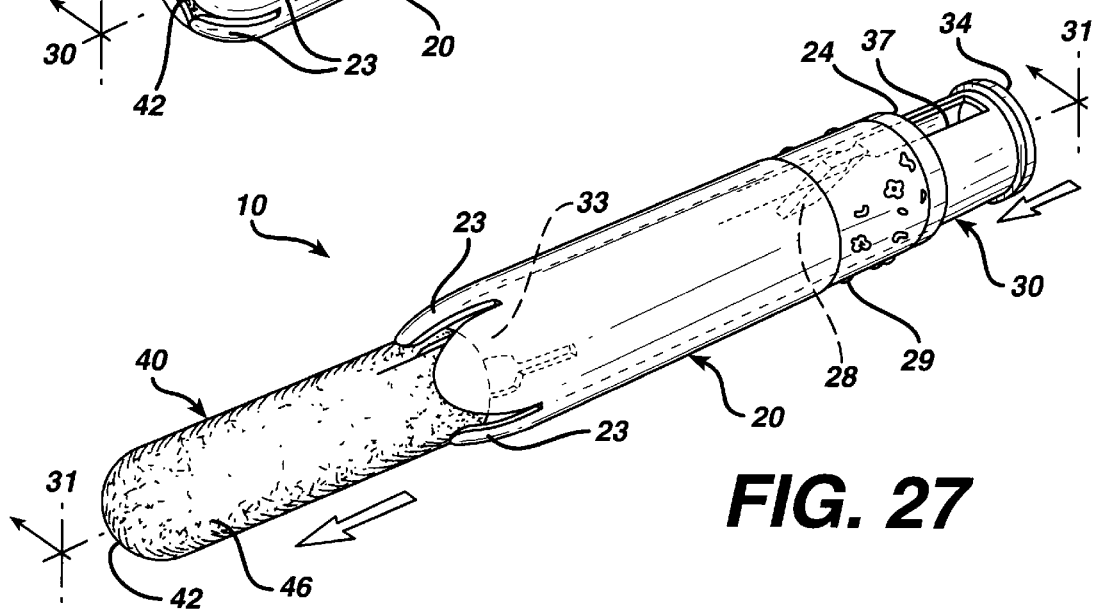
Figure 28:
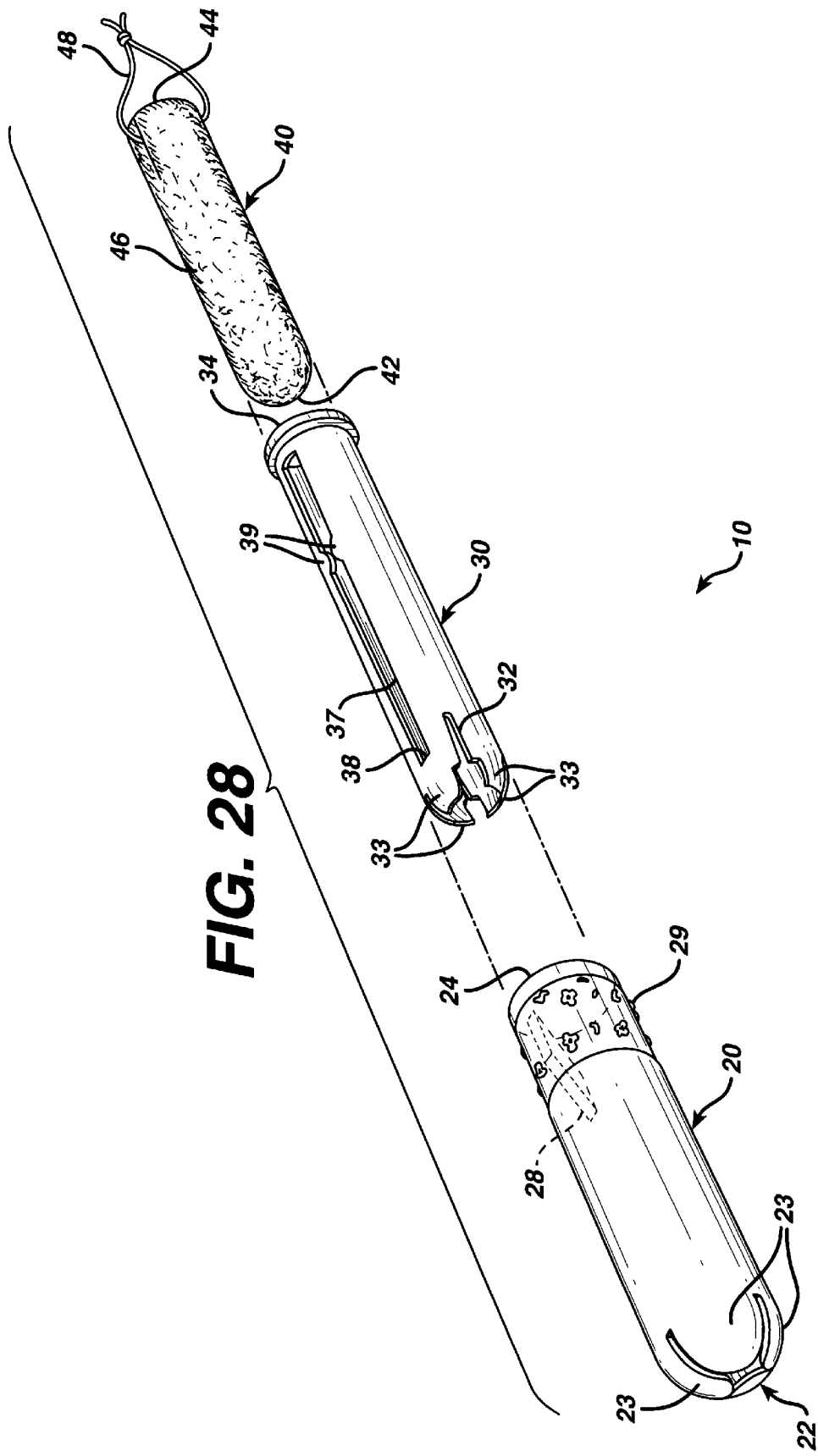
Figure 32:
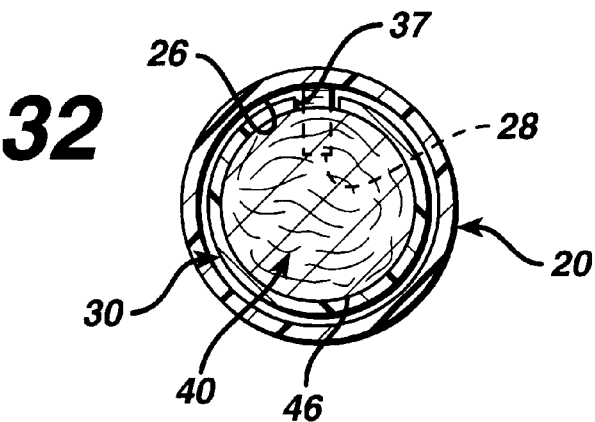
Figure 33:
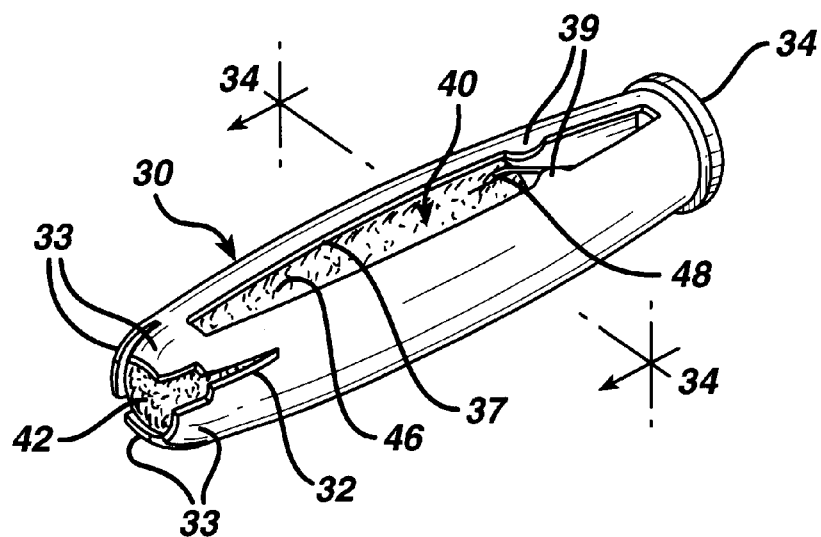
Figure 34:
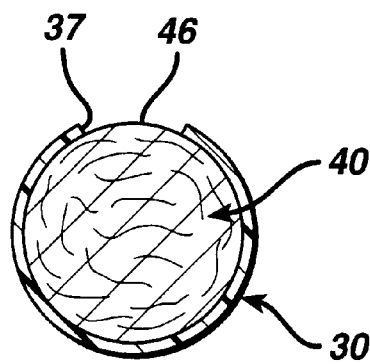

FIG. 26 is a perspective view of the applicator of FIG. 25 shown when the inner sleeve is being withdrawn almost completely out of the outer sleeve and positioned behind the tampon;

FIG. 27 is a perspective view of the applicator of FIG. 25 shown while the tampon is being expelled from the applicator;

FIG. 28 is an exploded perspective view of the applicator of FIG. 25;

FIG. 29 is a cross-sectional view taken along 5—5 of FIG. 25;

FIG. 30 is a cross-sectional view taken along 6—6 of FIG. 26;

FIG. 31 is a cross-sectional view taken along 7—7 of FIG. 27;

FIG. 32 is a cross-sectional view taken along 8—8 of FIG. 25;

FIG. 33 is a perspective view of the inner sleeve showing expansion of the tampon;

FIG. 34 is a cross-sectional view taken along line 10—10 of FIG. 33.

FIGS. 1 to 11 illustrate a first embodiment of a tampon applicator 50, which is composed of an essentially cylindrical outer sleeve 51 as well as an essentially cylindrical inner sleeve 52 and a tampon 53 with withdrawal cord 54 arranged in the inner sleeve. The outside diameter of the inner sleeve 52 is dimensioned smaller than the inside diameter of the outer sleeve 51, so that the inner sleeve 52 is mounted so as to be coaxially displaceable in the outer sleeve 51. The inner sleeve 52 is provided with an axial longitudinal slit 55 which is closed at the front and at the rear. The tampon 53 is coaxially enclosed by the inner sleeve 52, the withdrawal cord 54 extending through the interior of the inner sleeve 52 and out of the rear end thereof. A toroidal grip 56 on the periphery of the rear end of the inner sleeve 52 serves to grip and almost completely withdraw the inner sleeve 52 out of the rear end of the outer sleeve 51 in order to be able to transfer the tampon 53 into the outer sleeve 51, and from there introduce it into the body cavity.

According to FIGS. 1 and 2, the outer sleeve 51 is provided with a tongue-shaped retention element 60, the rear end of which is connected to the rear half of the outer sleeve 51, and which, at its free front end, projects through the longitudinal slit 55 of the inner sleeve 52 into the interior thereof and lies against the rear end of the tampon 53. When the inner sleeve 52 is withdrawn out of the rear end of the outer sleeve 51, the tampon 53 is consequently held in place by the retention element 60 and transferred into the outer sleeve 51.

According to the invention, the retention element 60 is provided with one part of a locking mechanism, the other part of which is formed in this first embodiment of the tampon applicator by the inner sleeve 52. The two parts of the locking mechanism interact with one another here in such a manner that, in its engaged position, the retention element 60 is locked in the inner sleeve 52. The one part of the locking mechanism formed by the retention element 60 in the locked state overlaps the part of the locking mechanism formed by the inner sleeve 52 and, when the latter is locked, grips under the part of the locking mechanism formed by the inner sleeve 52 in a locking manner.

The locking part of the retention element 60 consists, according to FIGS. 5 and 6, of a longitudinal segment of the same which is widened with respect to the longitudinal slit 55 in the inner sleeve 52 and forms a detent plate 65. The detent plate 65 is arranged at the front end of a shank 61 of the retention element 60, which is connected to the rear part of the outer sleeve 51. It can be seen from FIGS. 2 and 5 that the detent plate 65 is spade-shaped, its two side parts 68, 69, which project laterally beyond the width of the shank 61, gripping with transverse shoulders 70, 71 under the longitudinal edges 55a, 55b of the longitudinal slit 55 in the locking position illustrated in FIG. 1. The width of the shank 61 is approximately dimensioned as wide as or slightly narrower than the width of the longitudinal slit 55.

The wall of the rear part of the outer sleeve 51, from which the retention element 60 freely projects into a through-opening 58 in the wall of the outer sleeve 51 paraxially to the central longitudinal axis of the same, is reinforced in comparison to the wall thickness of the outer sleeve according to FIGS. 1 and 4. This reinforcement consists of an outer, longitudinally extending rib 59, which extends between a toroidal grip 62 on the periphery of the rear end of the outer sleeve 51 and the rear end of the through-opening 58 of the outer sleeve 51. The width of the reinforcing rib 59 corresponds approximately to the width of the through-opening 58 in the outer sleeve 51, such as is shown in FIGS. 2 and 6. The inner faces of the reinforcing rib 59 and of the retention element 60, in the unlocked position thereof, lie flush with the cylindrical inner wall of the outer sleeve 51. The retention element 60 forms a continuation of the reinforcing rib 59 and has the same wall thickness as the latter. The rear end of the shank 61 forms a bending axis 57 (FIGS. 1 and 2) of the retention element 60. The through-opening 58 and the retention element 60 may thus be produced from plastic in one work process by injection molding. As a result of the greater wall thickness of the reinforcing rib 59, the retention element 60 attains a bending strength which ensures a reliable retention but above all also a reliable transfer of the tampon 53 out of the inner sleeve 52 into the outer sleeve 51 when the inner sleeve 52 is withdrawn out of the rear end of the outer sleeve 51. As a result of the mechanical locking at the underside of the longitudinal edges 55a, 55b of the longitudinal slit 55, in this case the retention element 60 with its detent plate 65 maintains the position shown in FIG. 1.

Spreader strips 66, 67 protrude inwards from the inside of the parallel longitudinal edges 55a, 55b of the rear part of the longitudinal slit 55, which spreader strips enlarge the angle of action of the detent plate 65 of the retention element 60 into the interior of the inner sleeve 52, as FIGS. 1, 3, 8 and 10 show. According to FIGS. 1 and 6, the spreader strips 66, 67 extend essentially over the length of the through-opening 58, that is to say from the rear end of the inner sleeve 52 to slightly beyond the front end of the through-opening 58. It should be appreciated that, depending on the height of the spreader strips 66, 67 and/or the length of the detent plate 65, the angular position and hence the depth of engagement of the detent plate 65 into the interior of the inner sleeve 52 can be influenced in such a way that the retention and the pushing out of the tampon 53 out of the inner sleeve 52 into the outer sleeve 51 is at all times ensured.

As FIGS. 2 and 9 show, two longitudinal segments 63, 64 are dimensioned at the rear end of the longitudinal slit 55 of the inner sleeve 52 narrower than the width of the shank 61 of the retention element 60. The longitudinal edges 55a, 55b of the longitudinal slit 55 lies opposite one another in pairs in the form of arcs 72, 73 and 74, 75 and cause such a constriction of the longitudinal slit 55 that the shank 61 of the retention element 60, which is wider in contrast, can only be moved through the accurately constricted longitudinal segments 63, 64 of the longitudinal slit 55 by overcoming a friction resistance. Located between the two longitudinal segments 63 and 64 is a longitudinal segment 76 which has the normal width of the longitudinal slit 55. This longitudinal segment 76 accommodates the shank 61 of the retention element 60 in the relative position between outer sleeve 51 and inner sleeve 52 shown in FIGS. 1 and 2. This position of the sleeves 51, 52 with respect to one another corresponds to the initial position of the tampon applicator 50, in which the latter is supplied to the end user.

FIGS. 4 and 7 in particular show that the outer sleeve 51 is provided at the front end with six flexible lips 77 which are arranged at a distance from one another in the circumferential direction, which are inclined towards the longitudinal axis of the outer sleeve 51 and are outwardly arcuate, but which leave an opening 78 free in the middle. These flexible lips 77 are greatly rounded in each case at their outer edge and facilitate the introduction of the outer sleeve 51 of the tampon applicator 50 into the body cavity.

Figure 3:
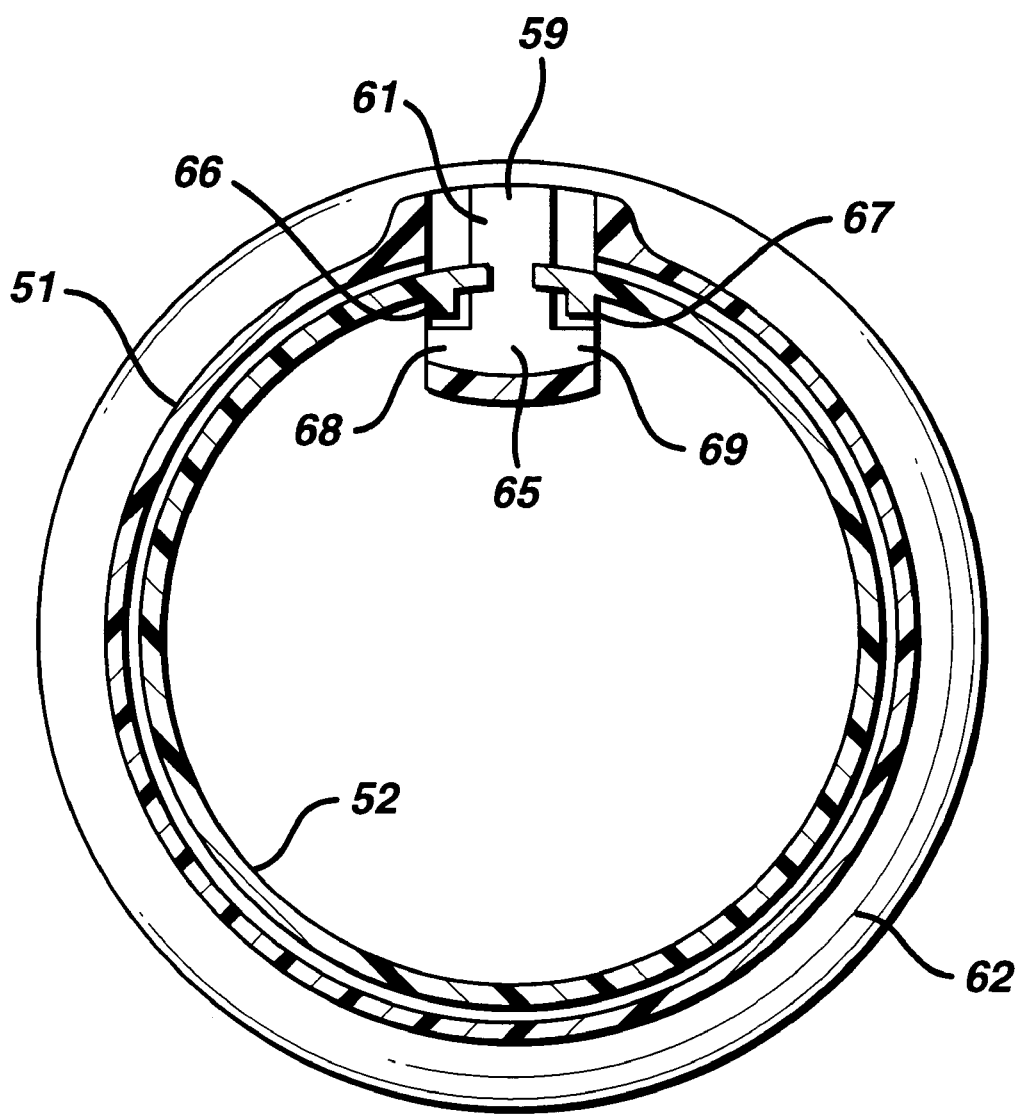
FIG. 3 shows a cross-section III—III in FIG. 2 on a larger scale.
Figure 10:
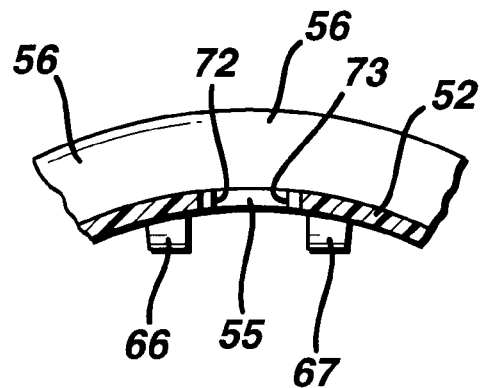
FIG. 10 shows a partial cross-section X—X in FIG. 8 on an enlarged scale.
Figure 11:
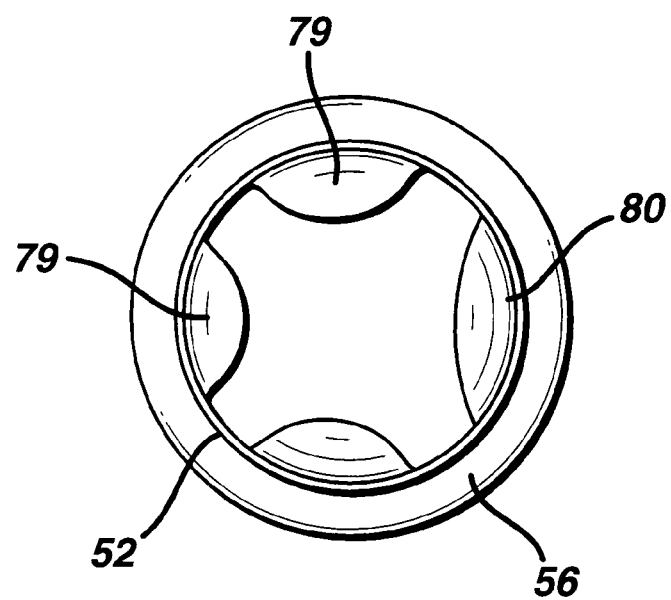
FIG. 11 shows a front view of the inner sleeve in FIG. 9.

In a similar manner, according to FIGS. 8, 9 and 11, the front end of the inner sleeve 52 is provided with a plurality of flexible lips 79, of which, however, one lip 80 differs by being dimensioned wider than the through-opening 58 in the outer sleeve 51, although exactly the same length as the other lips 79, as is shown in FIG. 9. Consequently, when the inner sleeve 52 is displaced, the lip 80 can glide over the region of the through-opening 58 in the outer sleeve 51.

FIG. 9 furthermore, shows that the front end of the longitudinal slit 55 extends beyond the cross-sectional plane of the inner sleeve 52, from which the lips 79, 80 project forwards, into the lip 80. The length of the lip 80 from the front end of the longitudinal slit 55 and the front end of the lip 80 is dimensioned smaller than the length of the front detent plate 65 of the retention element 60. This ensures that the front end of the detent plate 65 protrudes completely beyond the lip 80 of the inner sleeve 52 when the inner sleeve 52 is drawn back up to the stop of the front end of the longitudinal slit 55 on the shank 51 of the retention element 60. As a result, when the inner sleeve 52 is pulled back, the tampon 53 is completely transferred out of the inner sleeve 52 into the outer sleeve 51 and is subsequently pushed out of the outer sleeve 51 with the aid of the inner sleeve 52, which is then acting as slider after the introduction into the body cavity.

The lips 79, 80 of the inner sleeve 52 form a resilient stop for the insertion end of the tampon 53. The distance between the resilient lips 79, 80 and the tip of the retention element 60 projecting into the inner sleeve 52 is dimensioned slightly smaller than the length of the tampon 53, so that the tampon 53 in the inner sleeve 52 is held by the resilient lips 79, 80 with elastic pre-tension against the retention element 60.

FIGS. 12 to 24 show the second embodiment of a tampon applicator 150 according to the invention. The tampon applicator 150 is composed of an essentially cylindrical outer sleeve 151, an essentially cylindrical inner sleeve 152 with an outside diameter which is dimensioned smaller than the inside diameter of the outer sleeve 151 so that it is displaceable. The inner sleeve 152 is provided with an axial longitudinal slit 155, closed at the front and rear, with parallel longitudinal edges 155a, 155b. A tampon 153 with a withdrawal cord 154 is coaxially enclosed by the inner sleeve 152. A grip 156 at the rear end of the inner sleeve 152 serves to grip and almost completely withdraw the inner sleeve 152 out of the rear end of the outer sleeve 151. A tongue-shaped retention element 160 is connected with its rear end to the rear part of the outer sleeve 151, and with its free front longitudinal segment projects through the longitudinal slit 155 of the inner sleeve 152 into the interior thereof. The retention element 160 lies against the rear end of the tampon 153 so that, when the inner sleeve 152 is withdrawn from the outer sleeve 151, the tampon 153 is held in place by the retention element 160 and transferred into the outer sleeve 151, and can be pushed out of the latter into the body cavity by means of the inner sleeve 152.

The retention element 160 is provided with one part of a locking mechanism, the other part of which is formed in this embodiment by the outer sleeve 151, the two parts of the locking mechanism interacting in such a manner that, in its engaged position, the retention element 160 is locked in the inner sleeve 152 with respect to the outer sleeve 151. The one part of the locking mechanism formed by the retention element 160 in the unlocked state overlaps the part of the locking mechanism formed by the outer sleeve 151 and in the locked state grips under said part with a locking effect.

Figure 15:
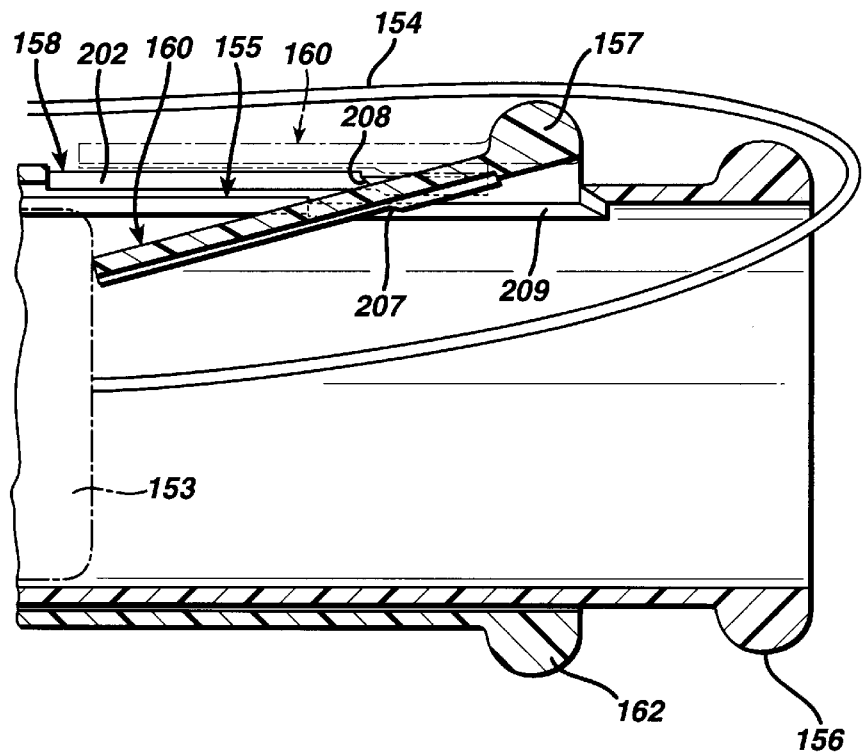
FIG. 15 shows the locked retention plate in FIG. 14 on an enlarged scale.
Figure 16:
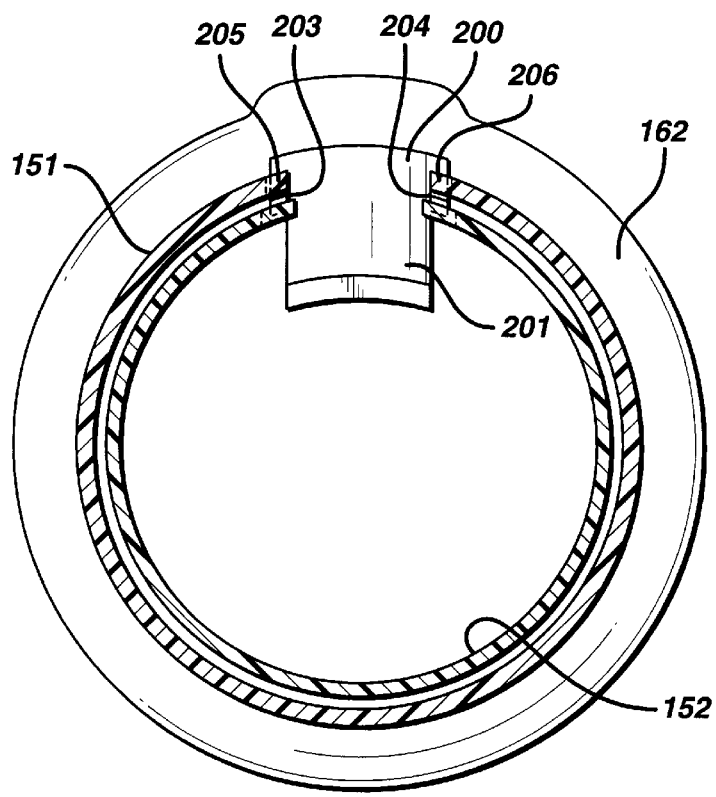
FIG. 16 shows a cross-sectional XVI—XVI in FIG. 12 on an enlarged scale.
Figure 18:
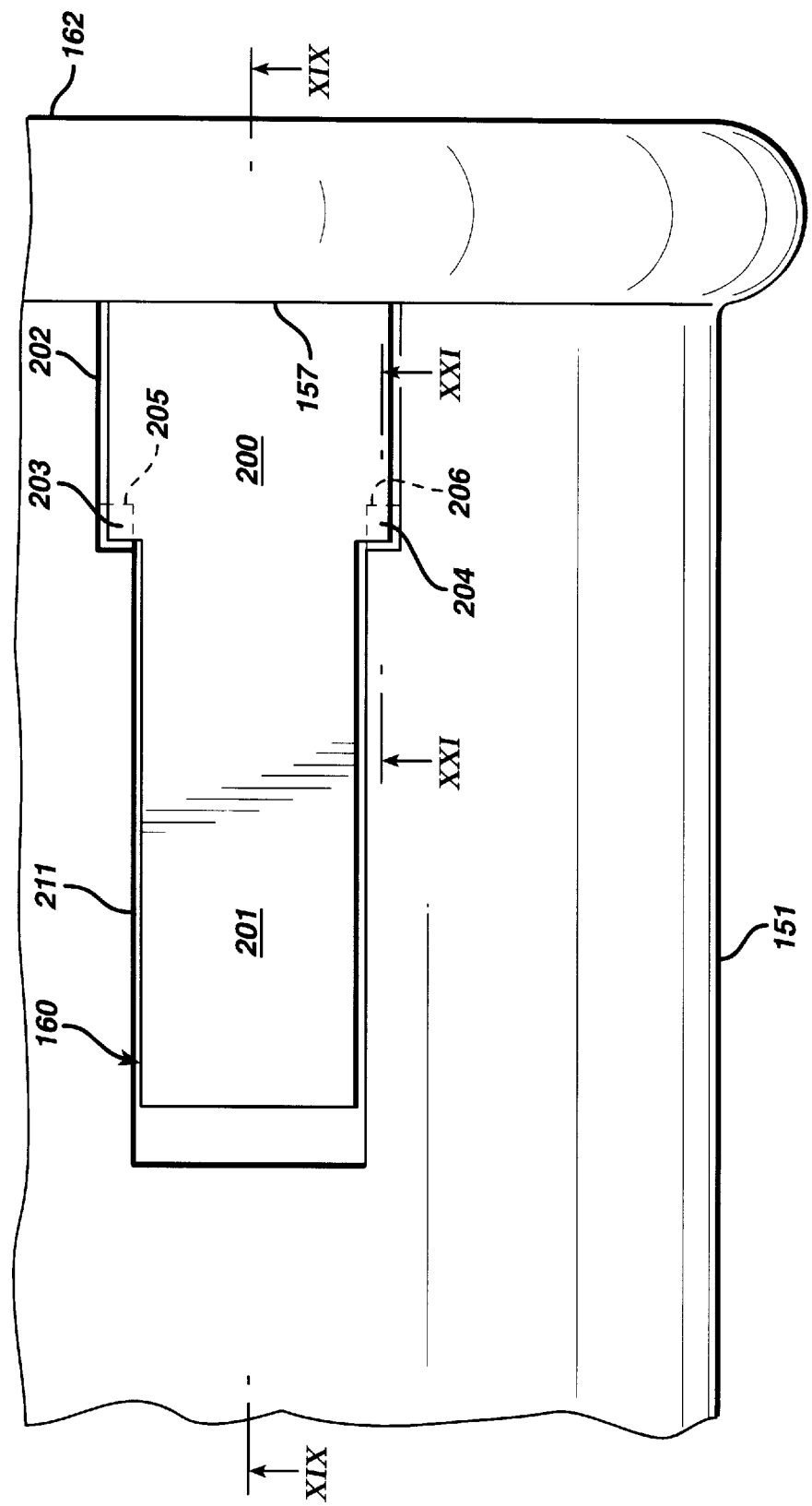
FIG. 18 shows a partially cutaway plan view of the outer sleeve with retention element on an enlarged scale.

As FIGS. 15 and 19 show, the retention element 160 extends in the unlocked state from the toroidal grip 162, forming a flexible bending axis 157 of the retention element 160, on the periphery of the rear end of the outer sleeve 151 freely forwards outside a through-opening 158 for the retention element 160 in the outer sleeve 151 paraxially to the latter. In the base region, the retention element 160 is provided with a detent plate 200 as locking part which interacts with rim parts of the through-opening 158 in the outer sleeve 151 forming the other locking part in order to lock the retention element 160. The front longitudinal segment of the retention element 160 forms a detent tongue 201 which extends forwards from the middle of the front end of the comparatively wider detent plate 200 to a greater length than the latter. As a result, the detent plate 200 has at the front on either side in each case one shoulder 203, 204 (FIG. 18). The wall thickness the retention element 160 is dimensioned uniformly thick over its entire length, but thicker than the wall of the associated outer sleeve 151 so that the necessary bending and buckling strength is obtained, as is shown in FIGS. 14, 15 and 19.

The through-opening in the outer sleeve 151, generally denoted by the reference symbol 158, consists of a rear longitudinal segment 202 which is dimensioned wider and longer than the detent plate 200, as well as a narrower longitudinal segment 211 adjoining the latter at the front, which is dimensioned longer and wider than the detent tongue 201. As is particularly evident from FIGS. 13, 15, 18, 19 and 24, rim parts of the through-opening 158 form shoulders 205, 206 which, in the initial position of the retention element 160 shown in FIG. 18, lie under the shoulders 203, 204 of the detent plate 200. The mutually opposite faces of the shoulder pairs 203, 205 and 204, 206 are, as FIG. 21 shows, formed as slanted faces 207, 208, which form an acute angle of approximately 45° with the horizontal so that the detent process is facilitated when the retention element 160 is pushed into the inner sleeve 152.

According to FIG. 12, and in particular FIG. 13, the longitudinal slit 155 of the inner sleeve 152 is provided in the region of its rear end with a widening 209 which is dimensioned wider and longer than the rear wider longitudinal segment 202 of the through-opening 158 in the outer sleeve 152. The widening 209 continues in a front longitudinal segment 212 of the longitudinal slit 155, which is dimensioned narrower than the detent tongue 201.

As a result, besides the interlocking of the detent plate with the shoulder 203, 204 with respect to the shoulders 205, 206 of the outer sleeve 151, frictional forces between the longitudinal edges 213, 214 of the detent tongue 201 and the longitudinal edges 155a, 155b of the narrow longitudinal segment 212 of the longitudinal slit 155, must be overcome in order to bring the detent tongue 201 into the desired engaged position according to FIG. 12. The advantage of this arrangement is that, as a result of the frictional contact between the detent tongue 201 and the longitudinal edges 155a, 155b of the front longitudinal segement 212 of the longitudinal slit 155, the inner sleeve 152 is held fast in its position pushed into the outer sleeve 151, which is the most suitable position for transporting the empty tampon applicator. At the same time, this frictional contact between detent tongue 201 and longitudinal slit 155 in the inner sleeve 152 offers the possibility of arresting the retention element 160 in addition to, but possibly also without, the interlocking of shoulders of the retention element and the outer sleeve, in its engaged position in the inner sleeve.

As FIG. 24 shows, the longitudinal slit 155 in the inner sleeve 152 can, if appropriate, have the width of the widening 209 over its entire length. The longitudinal slit 155 can, however, also be constricted towards a front longitudinal segment 215, the width of which is dimensioned greater than the narrow longitudinal segment 211 of the through-opening 158 extending forwards from the wider longitudinal segment 202. In this way, the detent tongue 201 can be bent into the inner sleeve 152 without resistance because the locking only takes place between the detent plate 200 and the outer sleeve 151. The longitudinal slit 155 can also be oriented at an acute angle to the longitudinal axis of the inner sleeve 152 as shown in FIG. 22a.

According to FIGS. 12, 14 and 17, the outer sleeve 151 is provided at the front end with six flexible lips 177 which are inclined at an acute angle towards the central longitudinal axis of the outer sleeve 151, are outwardly arcuate and are arranged with regular spacing over the periphery of the outer sleeve 151. The edges of these lips 177 are greatly rounded. The front ends of the lips 177 surround a central opening 178.

These lips 177 again serve to facilitate introduction of the tampon applicator 150 into the body cavity and are bent flexibly outwards when the tampon 153 is pushed out.

According to FIGS. 12, 14, 17, 22 and 23, the inner sleeve 152 is provided at the front end with four flexible lips 179 which are arranged on the periphery equidistantly from one another and in each case merge into a front lip 161. The straight front edge 159 of the front lip 161 is directed perpendicularly with respect to the central longitudinal axis of the inner sleeve 152. In the assembled state of the tampon applicator 150, the front lips 161 extend beyond the front ends of the lips 177 of the outer sleeve 151 and grip under the latter, so that they extend inwards essentially parallel with respect to the longitudinal axis of the applicator with a slight outward arching. This form of the front lips 161 ensures that, when the inner sleeve 152 is withdrawn out of the outer sleeve 151, the lips 179 can glide smoothly over the surface of the tampon 153. This is true even if an attempt is made to push the tampon out of the applicator before the lips 179 lie against the rear end of the tampon 153. At with the first embodiment, the depth of insertion of the inner sleeve 152 into the outer sleeve 151 is limited by the abutting of its front lips 179 against the inside of the lips 177 of the outer sleeve 151.

As was mentioned in connection with FIGS. 21 and 22, in its initial position the retention element 160 is arranged coaxially with respect to the associated outer sleeve 151, but outside the envelope surface formed by the cylindrical surface of the outer sleeve 151. As a result, the outer sleeve 151 can be produced without an additional side form element and can be mounted by simple axial lifting movements and a continuous rotary movement. The engaging process of the retention element 160 can be initiated here by axially sliding a form ring over the outer sleeve 151. The sleeves preferably consist of plastic, polyethylene, polypropylene or the like. However, a plastic that is biodegradable, such as, for example, mixtures of polyhydroxyvaleric acid or polyhydroxyvaleric acid, or a material which dissolves in contact with water, such as, for example, polyvinyl alcohol, is preferably used for the sleeves so that environmental damage need not be feared by the use of the applicator. If desired, the sleeves may also be made of paper or cardboard in a manner known to those of skill in the art.

It can be seen from the above description that the mechanical locking of the engaged position of the retention element into the interior of the inner sleeve offers the necessary reliability for a problem-free retention and a complete transfer of the tampon out of the inner sleeve into the outer sleeve, so that the tampon can be introduced quickly and reliably into the body cavity at the desired time. Finally, the described locking types of the retention element may also be combined with one another if necessary.

In a third preferred embodiment, shown in FIGS. 25–34, the tampon applicator is composed of a substantially cylindrical outer sleeve having at least one retention element protruding into the interior of the outer sleeve along the longitudinal axis of the outer sleeve. The inside surface of the outer sleeve may contain a plurality of retention elements. The outer sleeve is preferably provided with a gripping portion, circumferentially surrounding the rear portion of the outer sleeve, which aids in positioning the tampon applicator without slipping from the fingers of the user. Preferably, the gripping portion is patterned so as to provide non-slip areas. The front of the outer sleeve contains a slotted area and lips which are inward toward the central longitudinal axis of the outer sleeve. Preferably, the front portion is dome-shaped and the slot or slots are maintained in a rounded configuration so as to provide comfort for the user.

The inner sleeve of the tampon applicator of this preferred embodiment has an outside diameter dimensioned smaller than the inside diameter of the outer sleeve such that it is coaxially displaceable within the outer sleeve. The inner sleeve contains at least one axial longitudinal slit along its longitudinal axis, closed at the front and rear. The longitudinal edges of the longitudinal slit approach each other toward the front of the inner sleeve so as to form a tapered slit. The slit may be positioned at an acute angle to the longitudinal axis. The inner sleeve may contain a plurality of slits so long as the integrity of the sleeve structure is maintained.

A tampon plug with a withdrawal cord is coaxially enclosed by the inner sleeve. Preferably, the tampon plug is composed of relatively low-density absorbent material. Generally, tampon plugs may be composed of material having a higher density, i.e. about 0.6 g/cm$^3$. The novel construction of the tampon applicators allows the use of low-density tampon plugs having densities of less than about 0.35 g/cc. High-density tampon plugs may be uncomfortable to wear and may not absorb body fluid quickly enough to avoid staining and leakage.

The front of the inner sleeve is formed in such a configuration containing a slot or slots which allow the front of the inner sleeve to open in order to permit easier expulsion of the tampon plug from the inner sleeve. The slots form lips which arc toward the central longitudinal axis of the inner sleeve. The length of the slots should extend toward the rear end of the inner sleeve further than the front-most point of the tapered longitudinal slit. This permits the low density tampon plug to expand during storage and prior to use, and does not restrict the plug's diameter at any point along its circumference or axis. This construction also permits the plug to be expelled easily from the inner sleeve. Because of their low density, low-density tampons are likely to expand during the time between manufacture and use. Using a construction which permits expansion of the plug along the length of the plug results in the rear portion of the plug having the same diameter or smaller than the front portions of the plug and the inner sleeve. This permits easier passage through the front of the inner sleeve than if the rear of the tampon plug had expanded to a greater diameter than the front of the inner sleeve.

The tampon plug is preferably made of a low density absorbent material such as wood pulp, rayon, cotton, other cellulose products, and other absorbent materials. Preferably, the tampon plug is compressed radially, longitudinally and laterally in order relatively to increase its density such that insertion into the inner sleeve is easy. During storage, and prior to use, the plug resides in the inner sleeve piece of the tampon applicator which is cocoaxially inserted into the outer sleeve of the tampon applicator.

When the user desires to insert the tampon, she extends the inner sleeve away from the body. As she pulls the inner sleeve away from the body, the plug is retained in the outer sleeve by the retention element of the outer sleeve.

The tapered slit maintains the position of the inner sleeve until insertion. The user then grasps the outer sleeve at the rear end and pushes the inner sleeve so as to force it to expel the tampon plug through the slots at the front of the outer sleeve and into the vagina.

FIGS. 25, 26 and 27 illustrate a preferred embodiment of the tampon applicator of this invention, respectively, prior to withdrawing the inner sleeve, after withdrawing the inner sleeve and after the insertion stroke, i.e., pushing the inner sleeve forward in order to expel the tampon plug. Tampon applicator 10 consists of outer sleeve 20 and inner sleeve 30. Outer sleeve 20 has a gripping portion 29 at its rear end. Gripping portion 29 contains a relief pattern to provide a substrate for gripping by the user that will not slip from her fingers. The relief pattern of gripping portion 29 preferably does not protrude above the circumference of outer sleeve 20 or ring 24. Ring 24 is slightly raised above the level of the relief pattern so as to aid in positioning the user's fingers on outer sleeve 20. Preferably, ring 24 extends only to the same circumferential height as that of the out sleeve 20 so as to aid in stacking of the applicators in mass production. Front end 22 of outer sleeve 20 consists bf a plurality of resilient lips 23. Resilient lips 23 are preferably petal-shaped so as to increase the comfort of inserting the tampon assembly into the vagina.

Tampon applicator 10 is also provided with inner sleeve 30. Inner sleeve 30 has a tapered longitudinal slit 37 and a ring 35 around the periphery of its rear end 34. Ring 35 is slightly raised above the plane of the inner sleeve surface in order to facilitate the user's grasping inner sleeve 30 prior to insertion.

Although not depicted in FIG. 25, a tampon plug is retained, in storage, in inner sleeve 30.

FIG. 26 illustrates a tampon applicator of this invention as it appears after withdrawal of inner sleeve 30 toward the rear of the tampon applicator, as indicated by the arrow. FIG. 26 illustrates detents 39 which serve to retain inner sleeve 30 in position during storage and prior to use and to lock retention element 28 after expulsion. Inner sleeve 30 is withdrawn rearwardly from outer sleeve 20, depositing tampon plug 40 in outer sleeve 20. Tampon plug 40 is depicted in phantom in its position in outer sleeve 20. Tampon plug 40 is retained in position by retention element 28, located on the inner surface of outer sleeve 20.

Tapered longitudinal slit 37 is about the same width or slightly narrower at its front end than the width of retention element 28. This construction results in a stable relationship between tapered slit 37 and retention element 28. It enables inner sleeve 30 to lock in the withdrawn position without wobbling. This construction results a smoother insertion stroke.

FIG. 27 illustrates the tampon applicator of this embodiment after the insertion stroke has been made. Inner sleeve 30 is pushed forward, as depicted by the arrow. Because the circumference of tampon plug 40 is greater than that of resilient lips 33 of inner sleeve 30, tampon plug 40 is propelled forward and expelled through resilient lips 23 and out through the front end of outer sleeve 20.

FIG. 28 depicts tampon plug 40 having an outer surface 46. Tampon 40 has a withdrawl cord 48. Withdrawal cord 48 may be inserted through the tampon plug 40 transversely after tampon plug 40 is formed.

Inner sleeve 30 has a ring 35 around the periphery of the rear end 34 that facilitates the grasping of inner sleeve 30 by the user. At the front of inner sleeve 30 there is at least one slot 32. When there is only one slot 32 in the front end, resilient lip 33 may be an arcuate surface that is one-third, one-half or any fraction of the curved front end of the inner sleeve. In FIG. 28 four slots 32 and four resilient lips 33 are shown.

Slots 32 shown in FIG. 28 are wider toward the front of inner sleeve 30 than they are at their posterior ends. Preferably, he length of slots 32 extends beyond the frontmost end of tapered longitudinal slit 37. Slots 32 may be of uniform width or may be wider at their posterior end. Alternatively, the width of the slot 32 may vary irregularly. In one preferred embodiment, depicted in FIG. 28, slots 32 are "stepped". Employing a step-shaped slot contributes to the benefit of decreasing the force required to withdraw inner sleeve 30 from outer sleeve 20 prior to the insertion stroke.

The rectangular shape of slots 32 as shown in FIG. 28 may also be changed. The slots 32 may be triangular, rounded or of any geometric shape so long as resilient lips 33 are formed and slots 32 are open at the front end of inner sleeve 30.

Likewise, the shape and width of tapered longitudinal slit 37 may vary. However, in the preferred embodiment, as shown in FIG. 28 the length of the slit should extend along at least 50% of the length of the inner sleeve. The width of tapered longitudinal slit 37 should be approximately equal to or less than the width of the retention element 28 of outer sleeve 20. Detents 39 are optionally present in tapered longitudinal slit 37.

Outer sleeve 20 has a front end 22 composed of arcuate resilient lips 23 which are together toward the central longitudinal axis of outer sleeve 20. In FIG. 29 is depicted the inner surface 26 of outer sleeve 20, which has a retention element 28 extending through tapered longitudinal slit 37 toward the interior of the applicator. The shape of retention element 28 is preferably an elongate parallelogram that is oriented at an acute angle to inner surface 26 of outer sleeve 20. However, any shape or size projection that is capable of extending into longitudinal slit 37 and retaining tampon 40 in place could be used in the tampon applicator of this invention.

Outer sleeve 20 may, optionally, have at least one longitudinal slit 19 which may allow tampon 40 additional room to expand. However, longitudinal slits additional to slits provided for engagement with retention element 28 may not be juxtaposed with one another so as to maintain the structural integrity of the inner sleeve.

The tapered longitudinal slits on either the inner or outer sleeve may be axial longitudinal slits like the one shown in FIGS. 25, 26, 27, 28 and 33 or they may be oriented at an acute angle to the longitudinal axis of the sleeves. In fact, in such embodiments in which the slits are positioned at an acute angle to the longitudinal axis the sleeves will expand evenly throughout the length of the applicator because of the torque caused by placing the slit at angle with respect to the longitudinal axis. In cases in which the tapered longitudinal slit is aligned with the longitudinal axis as it is in FIG. 33, the center portion of the applicator tends to expand more than front end 22 or rear end 34. As is also shown in FIG. 33, though, slots 32 also permit expansion in front end 42. So long as slots 32 extend longitudinally past the foremost end of longitudinal slit 37, the degree of expansion of front end 42 will be approximately equal to expansion of the central portion of the tampon plug. With this tolerance for expansion in the front end of the tampon plug, the central portion may be expelled through the inner sleeve because the circumference of the plug and that of the inner sleeve will be approximately the same.

The effect of radial expansion of low density tampon plugs and the interplay between the expansion and slits 37 and slots 32 in accommodating that expansion is illustrated by the differences between the width of longitudinal slit 37 in FIG. 32 and its width in FIGS. 33 and 34 after it has expanded.

Retention element 28 may be wider than the width of tapered longitudinal slit 37, thus providing another force which acts to push tapered longitudinal slit 37 apart, and creating more space into which tampon plug 40 may expand.

FIGS. 25 and 29 show tampon applicator 10 in a pre-insertion mode in which inner sleeve 30 is telescoped axially away from the outer sleeve 20. Retention element 28 retains the tampon plug 40 in the front end of inner sleeve 30. When inner sleeve 30 is pulled in the rear direction as far away from the outer sleeve as possible, its front end is held within the outer sleeve 20 by the same retention element 28 that keeps the tampon plug in front end 22 of the outer sleeve in FIGS. 26 and 30. Inner sleeve 30 is now in position to push tampon plug 40 through resilient lips 23 of front end 22 of outer sleeve 20.

Then, as shown in FIGS. 30 and 31 resilient lips 33 in the front of inner sleeve 30 curve toward the center of rear end 44 of tampon plug 40 so that they may be used to push tampon plug 40 through front end 22 of outer sleeve 20.

What is claimed is:

1. A tampon applicator comprising:
   (a) an essentially cylindrical outer sleeve having a front end and a rear end with a toroidal grip, an inside diameter, and a through opening proximate the rear end, the through opening having rim parts having internally-facing shoulders extending transversely to a longitudinal axis of the through opening;
   (b) an essentially cylindrical inner sleeve defining an interior portion thereof with an outside diameter that is smaller than the inside diameter of the outer sleeve, the inner sleeve being mounted coaxially within the outer sleeve, having a front end and a rear end corresponding to the front and rear ends of the outer sleeve when the inner sleeve is inserted into the outer sleeve in a nested position, the inner sleeve also being provided with a longitudinal slit aligned with the through opening in the outer sleeve and which is closed at each end of the inner sleeve;
   (c) a tampon plug which is coaxially enclosed by the inner sleeve and which has a front end and a rear end corresponding to the front end and rear end of the inner sleeve;
   (d) a grip at the rear end of the inner sleeve for gripping and almost completely withdrawing the inner sleeve out of the rear end of the outer sleeve; and
   (e) a tongue-shaped retention element having
      (i) a proximal end which is integrally connected to the outer sleeve proximate the rear end thereof so as to be bendable;
      (ii) a distal end which projects through the longitudinal slit of the inner sleeve into the interior portion thereof and which is capable of bearing against the rear end of the tampon plug when the inner sleeve is withdrawn out of the rear end of the outer sleeve, such that the tampon plug is held in place by the retention element and transferred into the outer sleeve; and
      (iii) a detent plate at said distal end having longitudinal sides and externally-facing shoulders on the longitudinal sides which extend transversely with respect to the longitudinal axis of the retention element in which the externally-facing shoulders engage the internally-facing shoulders of the rim parts of the through-opening in the outer sleeve;

wherein the engaged shoulders of the detent plate and the rim parts retain the distal end of the retention element in the interior portion of the inner sleeve when in the inner sleeve is in the nested position.

2. A tampon applicator according to claim 1 wherein the rear part of the outer sleeve to which the retention element is connected is stiffened by an external rib which extends between the rear end of the outer sleeve and the retention element.

3. A tampon applicator according to claim 2 wherein the retention element is a continuation of the reinforcing rib.

4. A tampon applicator according to claim 3 wherein the retention element has a shank portion disposed between its proximal and distal ends, and wherein a rear part of the longitudinal slit in the inner sleeve has first, second and third segments the first and second segments being dimensioned narrower than the shank of the retention element, the third segment lying between the first and second segments and being at least as wide as the shank and receiving the shank of the retention element.

5. A tampon applicator according to claim 4 further comprising spreader strips protruding radially inward from the longitudinal slit and increasing the angle at which the retention element extends radially inwardly into the interior of the inner sleeve.

6. A tampon applicator according to claim 5 wherein the inner sleeve is provided at the front end with a plurality of flexible lips tapered to the front which form an acute angle with the central longitudinal axis of the inner sleeve and which are outwardly arcuate, such that the front end of the longitudinal slit in the inner sleeve extends into a resilient lip of the same which is dimensioned wider than the through-opening in the outer sleeve.

7. A tampon applicator according to claim 1 further comprising means for retaining the inner sleeve in a predetermined axial relation to the outer sleeve, whereby the inner sleeve is prevented from being prematurely withdrawn from the outer sleeve.

8. A tampon applicator according to claim 7 wherein the retaining means comprises a detent formed in the longitudinal slit of the inner sleeve.

9. A tampon applicator according to claim 8 wherein the retention element has a longitudinally extending region disposed between its proximal and distal ends, and wherein the detent comprises the longitudinal slit in the inner sleeve having a first portion and second and third portions disposed fore and aft, respectively, of the first portion, the first portion having a width smaller than the width of the longitudinally extending region of the retention element and the second and third portions having a width at least as wide as the longitudinally extending region of the retention element.

10. A tampon applicator according to claim 1 wherein the distal end of the retention element is wider than the width of the longitudinal slit in the inner sleeve.

11. A tampon applicator according to claim 10 wherein the detent plate is spade-shaped.

12. A tampon applicator according to claim 1 further means for increasing the angle at which the retention element extends radially inwardly toward the longitudinal center line of the inner sleeve.

13. A tampon applicator according to claim 12 wherein the angle increasing means comprises a longitudinally extending strip protruding radially inwardly from the inside diameter of the inner sleeve and adapted to engage the distal end of the retention element.

14. A tampon applicator according to claim 1 wherein the retention element is reinforced with respect to the thickness of the wall of the outer sleeve.

15. A tampon applicator according to claim 1 where the shoulders of the detent plate and of the corresponding rim parts of the through opening in the outer sleeve have mutually matched slanted faces.

16. A tampon applicator according to claim 1 wherein a longitudinal segment of the longitudinal slit in the inner sleeve is dimensioned narrower than the retention element in such a way that the inner sleeve is held frictionally against the retention element.

17. A tampon applicator comprising:
   (a) an essentially cylindrical outer sleeve having an inside diameter:
   (b) an essentially cylindrical inner sleeve defining an interior portion thereof having an outside diameter that is smaller than the inside diameter of the outer sleeve, said inner sleeve being coaxially displaceable within said outer sleeve, having a front end corresponding to a front end of the outer sleeve and a rear end corresponding to a rear end of the outer sleeve when the inner sleeve is inserted into the outer sleeve in a nested position the inner sleeve comprising means for allowing radial expansion, said radial expansion means comprising (i) at least one longitudinal slit which is closed at each end, and (ii) at least one slot in the front end of said inner sleeve, said slot having front and rear ends and being open at the front end and closed at the rear end, the rear end of said slot being located rearwardly from the front end of said longitudinal slit;
   (c) a tampon plug having a density of less than about 0.35 c/cm$^3$ which is coaxially enclosed by the inner sleeve and which has a front end and a rear end corresponding to the front end and rear end of the inner sleeve;
   (d) a gripping surface at the rear end of the inner sleeve for gripping and almost completely withdrawing the inner sleeve away from the outer sleeve; and
   (e) a retention element, a proximal end of which is integrally connected to the outer sleeve proximate the rear end thereof and a distal end of which projects through the longitudinal slit of the inner sleeve and into the interior portion thereof and which is capable of bearing against the rear end of the tampon plug when the inner sleeve is withdrawn out of the rear end of the outer sleeve, such that the tampon plug is held in place by the retention element and transferred into the outer sleeve wherein said radial expansion means further comprises said at least one slot being step-shaped.

* * * * *